United States Patent
Lawson et al.

(10) Patent No.: US 7,722,755 B2
(45) Date of Patent: *May 25, 2010

(54) METHOD OF ELECTRO-CATALYTIC REACTION TO PRODUCE MONO ALKYL ESTERS FOR RENEWABLE BIODIESEL

(75) Inventors: J. Alan Lawson, Dublin, GA (US); Ahmed A. Baosman, Duluth, GA (US)

(73) Assignee: ECR Technologies, Inc., Dublin, GA (US)

( * ) Notice: Subject to any disclaimer, the term of this patent is extended or adjusted under 35 U.S.C. 154(b) by 1574 days.

This patent is subject to a terminal disclaimer.

(21) Appl. No.: 10/987,115

(22) Filed: Nov. 12, 2004

(65) Prior Publication Data

US 2005/0120621 A1    Jun. 9, 2005

Related U.S. Application Data

(60) Provisional application No. 60/519,677, filed on Nov. 12, 2003, provisional application No. 60/552,612, filed on Mar. 12, 2004, provisional application No. 60/613,283, filed on Sep. 27, 2004.

(51) Int. Cl.
*C25B 3/00* (2006.01)
*C07C 67/00* (2006.01)

(52) U.S. Cl. .............. 205/440; 205/352; 205/331; 554/30; 554/124; 554/169; 554/174

(58) Field of Classification Search .......... 554/124, 554/169, 174; 44/308, 388; 205/440, 441
See application file for complete search history.

(56) References Cited

U.S. PATENT DOCUMENTS

| | | | |
|---|---|---|---|
| 284,862 A | * | 9/1883 | Lackersteen ............ 205/352 |
| 353,566 A | * | 11/1886 | Lackersteen ............ 205/440 |
| 2,147,177 A | | 2/1939 | Seto et al. |
| 3,326,784 A | * | 6/1967 | Koehl, Jr. ............... 205/441 |
| 3,608,039 A | * | 9/1971 | Ross et al. ............... 204/167 |
| 3,835,006 A | | 9/1974 | Fujita et al. |

(Continued)

FOREIGN PATENT DOCUMENTS

CA    2131654    3/1996

OTHER PUBLICATIONS

Vines.org Encyclopedia, Information about Vinification, 2008, (abstract).*

(Continued)

*Primary Examiner*—Jafar Parsa
*Assistant Examiner*—Yate' K Cutliff
(74) *Attorney, Agent, or Firm*—Sutherland Asbill & Brennan LLP

(57) ABSTRACT

Methods, systems, and devices are provided for synthesizing one or more chemical products from a renewable oil, comprising the step of flowing a fluid which comprises a renewable oil through a high voltage electrical field effective to catalyze a chemical reaction involving the renewable oil. Examples of renewable oils include vegetable oils, animal fats, bio-oils, and combinations thereof. In one embodiment, the fluid further comprises an alcohol mixed with the oil, and the chemical reaction produces biodiesel and an etherified glycerin. In one embodiment, the biodiesel is further reacted to produce acetic acid.

34 Claims, 8 Drawing Sheets

U.S. PATENT DOCUMENTS

| | | |
|---|---|---|
| 4,013,524 A | 3/1977 | Tyssee |
| 4,028,201 A | 6/1977 | Tyssee |
| 4,164,506 A | 8/1979 | Kawahara et al. |
| 4,190,522 A | 2/1980 | Tra |
| 4,695,411 A | 9/1987 | Stern et al. |
| 4,698,186 A | 10/1987 | Jeromin et al. |
| 4,848,674 A | 7/1989 | Hunter |
| 5,225,581 A | 7/1993 | Pintauro |
| 5,238,538 A | 8/1993 | Jagannadh et al. |
| 5,476,971 A | 12/1995 | Gupta |
| 5,520,708 A | 5/1996 | Johnson et al. |
| 5,525,126 A | 6/1996 | Basu et al. |
| 5,578,090 A | 11/1996 | Bradin |
| 5,580,446 A | 12/1996 | Markham |
| 5,713,965 A | 2/1998 | Foglia et al. |
| 5,733,413 A | 3/1998 | Lawson |
| 5,891,203 A | 4/1999 | Ball et al. |
| 6,086,645 A | 7/2000 | Quigley et al. |
| 6,139,684 A | 10/2000 | Lawson et al. |
| 6,238,523 B1 | 5/2001 | Lawson |
| 6,248,230 B1 | 6/2001 | Min et al. |
| 6,440,057 B1 | 8/2002 | Ergun et al. |
| 2002/0121352 A1 | 9/2002 | Lawson et al. |
| 2003/0209539 A1 | 11/2003 | Dalton |

OTHER PUBLICATIONS

CN 86103016, Chen, et al. Wine maturing acceleratin involves electro-catalytic process using platinoum electtrodes to promote osication, reduduction and esterification process, 1986 (abstract 2 pages).*

Boocock, et al. *Biomass & Bioenergy*, 11(1): 43-50 (1996).

* cited by examiner

Linoleic acid C18:2 ω6

Alpha linolenic acid C18:3 ω3

METHOD OF ELECTRO-CATALYTIC REACTION TO PRODUCE MONO ALKYL ESTERS FOR RENEWABLE BIODIESEL

CROSS-REFERENCE TO RELATED APPLICATIONS

This application claims the benefit of U.S. Provisional Application No. 60/519,677, filed Nov. 12, 2003; U.S. Provisional Application No. 60/552,612, filed Mar. 12, 2004; and U.S. Provisional Application No. 60/613,283, filed Sep. 27, 2004. These applications are incorporated herein by reference.

BACKGROUND OF THE INVENTION

The field of this invention generally related to chemical production methods employing electro-catalytic reaction mechanisms, and more particularly, to methods and systems using vegetable oil and other non-petroleum oil feedstocks to make biodiesel, acetic acid, glycerol, select fatty acids and polymers, and the like.

Chemical syntheses are ubiquitous and important to numerous industries throughout the world, particularly the industries involved in the production of organic chemicals, polymers, pharmaceuticals, inorganic chemicals, and specialty chemicals. Due to the time and cost of various chemical synthesis processes, industries are always striving to improve current devices and methods for chemical synthesis; including for example, ways to reduce the time and cost of purification/separation steps involved, methods to decrease the energy cost of production, methods to increase overall product yields, and improvements in the efficiency of chemical synthesis.

Biodiesel

Fossil fuels, particularly coal, oil, and natural gas, are the primary fuels of industrialized society. However, the supply of fossil fuel is limited and non-renewable, and its use is believed to contribute to substantial environmental pollution and health issues. Based on some recent estimates of consumption rate, the U.S. will deplete its natural reserve of all fossil fuels by 2036, and by the year 2041, the entire planet will deplete its natural reserve of all fossil fuels if this same rate of consumption continues to grow. Furthermore, roughly 22 gigatons of carbon dioxide ($CO_2$) presently are being released into the atmosphere each year from use of fossil fuels, and more than 1.5 million tons of sulfur dioxide pollution are produced in the U.S. each year by vehicle engines burning fossil fuel. Because, the natural environment cannot rapidly reuse the $CO_2$, the amount of $CO_2$ in the atmosphere continues to increase. Thus, there is a tremendous resource and environmental burden to find alternative renewable energy sources to the non-renewable fossil fuel.

A viable alternative to fossil fuel is biodiesel, a renewable source of energy. Biodiesel (or bio-fuel) is the name for a variety of ester-based fuels (e.g., fatty esters) generally made from vegetable oils, such as soybean oil, canola or hemp oil, or sometimes from animal fats through a simple transesterification process. This renewable source is as efficient as petroleum diesel in powering unmodified diesel engine. Since the introduction of biodiesel fuel in South Africa prior to World War II, work has proceeded to increase its viability as a fuel substitute. Recent environmental and economic pressures have hastened the need to enhanced development of this renewable energy source.

Biodiesel offers many advantages. Biodiesel runs in any conventional, unmodified diesel engine; thus, no engine modifications are necessary. Biodiesel can be used alone or mixed in any amount with petroleum diesel fuel. For example, a 20% blend of biodiesel with (petroleum-based) diesel fuel is called "B20," a 5% blend is called "B5," and so on. This renewable fuel can be stored anywhere that petroleum diesel fuel is stored and all diesel fueling infrastructure including pumps, tanks and transport trucks can use biodiesel without modifications. In addition to the compatibility with diesel-based infrastructures, biodiesel can provide a net reduction in $CO_2$ emissions, and biodiesel produces no sulfur dioxide when burned. Furthermore, biodiesel is considered biodegradable and non-toxic.

Conventional biodiesel improves engine emissions in most categories when compared to pipeline petroleum diesel fuel. Blends containing higher concentrations of conventional biodiesel, however, disadvantageously show a proportional increase in emissions of nitrogen oxides ($NO_X$). For instance, it is well documented that use of a conventional biodiesel blended with petroleum diesel fuel in a 80% petroleum/20% biodiesel blend results in increased nitrous oxide emissions by 2 to 11%. Presently, $NO_X$ emissions are a significant limitation to the widespread adoption of biodiesel fuels.

Some researchers have sought to address the $NO_X$ issue by the addition of certain fuel additives to the biodiesel. For example, U.S. Pat. No. 5,578,090 to Bradin discloses a fuel additive composition including fatty acid alkyl esters and glyceryl ethers. The additive-containing fuel is made by a multi-step process that includes separation of glycerol from biodiesel, conversion of glycerol to glycerol ether, and then addition of the glycerol ether back into the biodiesel fuel. Other researchers describe controlling engine emission $NO_X$ by adding water to the fuel, which cools the combustion process and reduces the formation of $NO_X$. However, that process undesirably lowers fuel BTU value by replacing fuel with water. It would be desirable to provide a biodiesel fuel that would lower $NO_X$ emissions without lowering fuel BTU value, and to provide simpler and less expensive methods producing such fuels.

Conventional methods of producing biodiesel fuel or fuel additive use existing technologies that relate to surfactant manufacturing processes. These are widely known and practiced through out the industry. Traditionally, biodiesel is synthesized via transesterification, as exemplified in FIG. 1. Transesterification, in relation to biodiesel, involves taking a triglyceride molecule or a complex fatty acid, neutralizing the free fatty acids, removing the glycerin, and creating an alcohol ester. This is accomplished by mixing a wood alcohol, e.g., methanol, with sodium hydroxide to make sodium methoxide. This dangerous liquid is then mixed into vegetable oil. As the reaction proceeds, contaminant formation of glycerol and possibly some surfactant occurs. The entire mixture then settles, with glycerin on the bottom and methyl esters, or biodiesel, on top (supernatant). Expensive separation of these contaminants is required to produce pure methyl ester or biodiesel.

This typical industry process method includes the use of catalytic reactions with high temperature and pressure. The combined utilization of these factors is to excite electrons to migrate back and forth across the surface of the catalysis to drive the reaction process to completion. Process challenges include issues of improving the decontamination processes for regenerating the catalysis, reducing dependency on homogenous catalysis that produce unwanted species during the reaction, developing continuous large volume processes to help reduce costs, reducing environmental impact of decontamination processes, constructing better heterogeneous catalysis without dependency on rare earth materials, constructing a catalysis to work more efficiently with heavier crude oils, improving pharmaceutical process purity with better catalytic reactions, lower temperature and pressure requirements of catalytic reactions, improving surface pour area of catalysis to accept larger molecules, reducing contamination reactions inside the catalysis during production operations, researching to find catalysis that perform reactions in a shorter time period, and improving molecular bonding during catalytic reactions.

After the reaction, the unreacted methanol, or ethanol, and the catalyst must be removed to purify the methyl ester. The necessity of this further processing is the crux of the problem with conventionally produced biodiesel fuels: They are not cost competitive with petroleum diesel fuel in part due to the process expense. In fact, most biodiesel fuels are more than 1.5 times higher in production cost than petroleum derived diesel. Thus, there is a need in the industry for devices and methods which reduce the use of catalysts and increase useable byproducts, such as hydrogen gas in the production of biodiesel.

Another problem of conventional biodiesel fuel is the cost of refined oil. Crude vegetable oil has considerable free fats that react with the catalysis to form fuel contaminants, such as surfactant and glycerol. Therefore, crude vegetable oil is not a suitable oil source for conventional biodiesel production. These contaminants are costly to remove and formation must be avoided or reduced whenever possible. Conventional biodiesel production requires a homogenous catalysis that produces unwanted side reactions; however, such side reactions preferably should be minimized or eliminated from the process.

Reaction time for conventional batch processes of making biodiesel typically ranges from 1 to 8 hours, and separation time for contaminant removal adds 8 to 16 hours. Thus, a gallon of biodiesel requires about 24 hours of processing time. Some researches have attempted to alleviate the problem of the slow reaction rate. Examples include the use of non-reactive co-solvents, which converts the two-phase system into a single-phase system. For instance, Canadian Patent Application No. 2,131,654 discloses using simple ethers, such as tetrahydrofuran (THF) and methyltertiarybutylether (MTBE) as co-solvents. Molar ratios of alcohol to triglyceride of at least 4.5:1 and more preferably at least about 6:1 are disclosed, with typical ratios being in the range of 6:1 to 8:1. The reaction is further discussed by D. G. B. Boocock et al in *Biomass & Bioenergy,* 11(1): 43-50 (1996). However, this process still produced numerous byproducts which require expensive and time-consuming purification techniques. For these reasons, conventional processes are not economically competitive with petroleum diesel.

Various esterification processes are described in the art. Examples include U.S. Pat. No. 4,164,506 to Kawahara et al. (disclosing (a) esterification of free fatty acids in the presence of an acid catalyst, (b) allowing the product mixture to separate into a fat layer and an alcohol layer so as to obtain a refined fat layer, and (c) then subjecting the fat layer to transesterification with a base catalyst); U.S. Pat. No. 4,695,411 to Stern et al. (disclosing a multi-step reaction involving acid transesterification with alcohol in the presence of 1-60% water and separating a resulting glycerol phase, reducing the free acidity of the remaining ester phase and then transesterification in the presence of a base catalyst); U.S. Pat. No. 4,698,186 to Jeromin et al. (disclosing a process for reducing the free acid content of fats and oils by esterification with an alcohol in the presence of an acidic cation exchange resin); U.S. Pat. No. 5,525,126 to Basu et al. (disclosing esterification of mixtures of fats and oils by using a calcium acetate/ barium acetate catalyst, with undesirable process conditions of 200° C., 500 psi, and a reaction time of three hours); U.S. Pat. No. 5,713,965 to Foglia et al. (disclosing use of lipases to transesterify mixtures of triglycerides and free fatty acids, with reactions requiring 4 to 16 hours to reach conversion rates of 95%); and U.S. Pat. No. 5,520,708 to Johnson et al. (disclosing reaction of triglycerides with methanol in the presence of base to produce fatty acid methyl esters). Various carboxylation processes also are known. Examples include U.S. Pat. No. 5,476,971 to Gupta (disclosing reacting pure glycerol with isobutylene in the presence of an acid catalyst in a two phase reaction to produce mono-, di- and tri-tertiary butyl ethers of glycerol); U.S. Pat. No. 4,013,524 to Tyssee (disclosing method of electrolytic carboxylation and dimerization of olefinic nitrites, esters and amides); and U.S. Pat. No. 4,028,201 to Tyssee (disclosing a procedure for electrolytic monocarboxylation of olefinic nitriles, esters and amides in which the reaction is moderated by protons to direct it toward monocarboxylation); U.S. Pat. No. 5,225,581 to Pintauro (disclosing electrocatalytic process for hydrogenating an unsaturated fatty acid, triglyceride, or mixtures thereof as an oil or fat); U.S. Pat. No. 5,891,203 to Ball et al. (disclosing use of blends of diethanolamine derivatives and biodiesel as an additive for improving lubricity in low sulfur fuels and to fuels and additive concentrates comprising said lubricity additives.)

Examples of other fuel production methods are disclosed in U.S. Pat. No. 6,440,057 to Ergun et al., which discloses a method for producing fatty acid methyl ester, including compounding saturated and unsaturated higher fatty substances from at least one of vegetable and animal with an alkaline solution dissolved in alcohol to form a mixture, and in U.S. Pat. No. 6,248,230 to Min et al., which discloses a method for manufacturing cleaner fuels, in which NPC (Natural Polar Compounds), naturally existing in small quantities within various petrolic hydrocarbon fractions, are removed from the petrolic hydrocarbon. U.S. Pat. No. 6,086,645 to Quiqley discloses low sulfur fuel compositions, which exhibit improved lubricity compared to the low sulfur fuels alone.

Thus, there is a need for developing devices and methods to improve chemical reaction performance, particularly with respect to the production of biodiesel, while lowering production costs and yielding higher quality products. These improvements include efficiency improvements in conversion reactions, as well as final product purity, energy savings, and lowering production costs of biodiesel.

Polymerization

There also exists a need for improved devices and methods for efficient synthesis of polymers. Currently, many polymerization techniques in the art result in multiple reactions which require tedious separation and/or purification steps. Reducing the reaction steps such as purification and separation steps are invaluable to industries, saving millions of dollars in production cost and reaction time. For example, polyesters are important polymers with multiple usages; thus industries would benefit for an efficient synthesis technique. Thus, there is also a need in the industry for devices and methods for improving the efficiency and cost of production for the synthesis of polymers.

Surfactant

Another widely commercialized chemical industry relates to surfactants. A surfactant is a material that can greatly reduce the surface tension of water when used in very low concentrations. This material or molecule is made up of water soluble (hydrophilic) and water insoluble (hydrophobic) components. The hydrophobe may be for example the equivalent of an 8- to 18-carbon hydrocarbon, and can for example be aliphatic, aromatic, or a mixture of both. The synthesis of surfactant typically requires some form of catalyst, an oil or fat, and strong base such as sodium hydroxide. Similar to the syntheses described above, the current methods and devices for the production of surfactant requires several separation and/or purification steps and the use of catalysts, which can be toxic.

The sources of hydrophobes are normally natural fats and oils, petroleum fractions, relatively short synthetic polymers, or relatively high molecular weight synthetic alcohols. The hydrophilic groups give the primary classification to surfactants, and are anionic, cationic and non-ionic in nature. The anionic hydrophiles are for example carboxylates (soaps), sulphates, sulphonates and phosphates. The cationic hydrophiles may be for example some form of an amine product. The non-ionic hydrophiles associate with water at the ether oxygens of a polyethylene glycol chain. In each case, the hydrophilic end of the surfactant is strongly attracted to the water molecules and the force of attraction between the hydrophobe and water is only slight. As a result, the surfactant molecules align themselves at the surface and internally so that the hydrophile end is toward the water and the hydrophobe is squeezed away from the water.

Surfactants have wide commercial usage. Representative examples of surfactant usage include soaps, detergents, fabric softeners, shampoo, cosmetics (e.g., skin care formulations, sunscreens), environmental remediation (e.g., remediation of contaminated aquifers, soil stabilization, sludge treatment, enhanced oil/petroleum recovery and/or dispersants), mineral flotation, and medical applications (e.g., liposome drug delivery). It would be desirable to provide improved and more efficient processes and devices for surfactant synthesis.

Acetic Acid

Acetic acid ($CH_3COOH$) is a carboxylic acid, which is used in a variety of products and processes. Acetic acid is essential in widespread industrial applications from textile to herbicide industries. In one particular process, acetic acid is used in the manufacture of acetate esters, where it is used to make materials such as cellulose acetate (used in rayon and photographic film) and polyvinyl acetate (used in latex paints and wood glues). It is an ideal solvent for many organic compounds and some inorganic compounds. Chemically, acetic acid shares most of the properties of carboxylic acids in general, including the ability to react with alcohols and amines to produce esters and amides, respectively. In addition, it can react with alkenes to produce acetate esters. When heated above 440° C., it decomposes to produce carbon dioxide and methane, or to produce ketene and water.

Acetic acid is the chemical component that gives vinegar, typically 4-8% acetic acid by volume, its sour taste. Many countries require that the acetic acid found in vinegar be produced by natural fermentation rather than by non-biological means. Vinegar is manufactured by fermenting various starchy, sugary, or alcoholic foodstuffs with *Acetobacter* bacteria. Commonly used feed stocks include apple cider, wine, and grain or potato mashes. The vinegar is then distilled from the fermentation broth.

Industries producing acetic acid face expensive separation and purification challenges. Most acetic acid made for industrial uses one of three chemical processes: butane oxidation, acetaldehyde oxidation, or methanol carbonylation.

When butane is heated with air in the presence of various metal ions, including those of manganese, cobalt, and chromium, peroxides form and then decompose to produce acetic acid according to the chemical equation:

$$C_4H_{10} + 2\tfrac{1}{2}O_2 \rightarrow 2CH_3COOH + H_2O \qquad \text{EQ. 1}$$

Typically, the reaction is conducted at temperature and pressure conditions of 150° C. and 55 atm. Several side products are formed, including butanone, ethyl acetate, formic acid, and propionic acid. These must be removed after reaction to purify the product.

Under similar conditions and using similar catalysts used for butane oxidation, acetaldehyde can be oxidized by the oxygen in air to produce acetic acid $$CH_3CHO + \tfrac{1}{2}O_2 \rightarrow CH_3COOH \qquad \text{EQ. 2}$$

Using modern catalysts, this reaction can have an acetic acid yield greater than 95%. The major side products are ethyl acetate, formic acid, and formaldehyde, all of which have lower boiling points than acetic acid and are readily separated by distillation. Acetaldehyde oxidation is the second most widely-used method of acetic acid production, second only to methanol carbonylation.

In the methanol carbonylation reaction, methanol and carbon monoxide react to produce acetic acid according to the chemical equation:

$$CH_3OH + CO \rightarrow CH_3COOH \qquad \text{EQ. 3}$$

Because both methanol and carbon monoxide are relatively inexpensive, methanol carbonylation long appeared to be an attractive method for acetic acid production, and patents on such processes were granted as early as the 1920's. However, the high pressures needed (200 atm or more) discouraged commercialization.

Today the principal methods of producing acetic acid industrially, with greater than 60% of the world's total acetic acid output per year, comprise improved methods of carbonylation of methanol. Over the years, improvements in catalysis have increased the selectivity of the reaction and decreased the pressure and temperature requirements of the process. For example, in 1960, BASF introduced a commercial process using a cobalt catalyst, which operates at high temperatures and pressures (250° C. and 680 bar), with a selectivity of methanol to acetic acid of about 90%. In 1966, the Monsanto Company found that using a rhodium catalyst made the reaction possible under milder conditions (180° C., 30-60 bar), with a selectivity of about 99% relative to methanol. In 1995, BP Chemicals introduced the Cativa process, which is based upon an iridium catalyst, and boasts improved catalyst stability, better reaction rates, and reduced by-product formation. In all of these processes, however, an organometallic species must be present with the reactants for the reaction to proceed.

Typically, the catalyst is a homogenous catalyst, which is evenly dispersed in a liquid phase. This homogeneously catalyzed reaction proceeds at 22 bar and 192° C., where methanol and carbon monoxide react to form acetic acid as shown by EQ. 3. However, due to the complexity of the catalytic reaction, some of the intermediates are not converted to acetic acid. The main by-products are hydrogen gas, methyl acetate, acetaldehyde, propionic acid, and methyl iodide. Hydrogen is formed in the system by the water-gas shift reaction, $$CO + H_2O \rightarrow CO_2 + H_2 \qquad \text{EQ. 4}$$

which combines carbon monoxide and water to form carbon dioxide and hydrogen gas. This reaction consumes a minor amount of products, and proceeds since the reactor is at a high temperature and pressure.

Methyl acetate, an intermediate, can react with water to form acetic acid. This reaction requires the presence of a catalyst and the reaction temperature and pressure to proceed.

The following equation shows the reaction of the methyl acetate by-product to acetic acid when combined with water at reaction conditions.

$$CH_3COOCH_3 + H_2O \rightarrow 3/2 CH_3COOH + H_2 \quad \text{EQ. 5}$$

Propionic acid is the main impurity in the final product, since its chemical properties are similar to those of acetic acid. Propionic acid is generated from the carbonylation of ethanol, which can be present as an impurity in the methanol feed or from reduction of acetaldehyde by hydrogen in the system. The following equation shows the carbonylation of ethanol to form propionic acid.

$$CH_3CH_2OH + CO \rightarrow CH_3CH_2COOH \quad \text{EQ. 6}$$

Finally, as part of the interaction between the iridium catalyst and ruthenium promoter, iodine is added and removed from the iridium atoms. When the reactants are removed, the cycle is not complete and the methyl iodide results as a by-product. Methyl iodide is generated by the reaction of methanol with hydrogen iodide, which occurs at the end of the catalytic cycle. The following equation shows the formation of methyl iodide.

$$CH_3OH + HI \rightarrow CH_3I + H_2O \quad \text{EQ. 7}$$

It is important to recuperate this species, as it contains iodide that is vital to the catalytic cycle. In addition, methyl iodide is a hazardous material, so its recovery is not only advantageous, but a necessity in order to avoid hazardous emissions.

It therefore would be desirable to provide improved methods of acetic acid and glacial acetic acid syntheses, which would produces fewer unusable byproducts and which would obviate or diminish the need to use organometallic catalysts.

Fatty Acids

A variety of fatty acids are known, and some fatty acids are essential to the human body. Some of these essential fatty acids cannot be made by the body and thus must be consumed as part of the human diet. Two essential fatty acids are polyunsaturated fatty acids (PUFAs) that cannot be made in the body: linoleic acid and alpha-linolenic acid. (See FIGS. 2 and 3.) Within the body, both of these can be converted to other PUFAs, such as arachidonic acid, or omega-3 fatty acids eicosapentaenoic acid (EPA) and docosahexaenoic acid (DHA). In the body, polyunsaturated fatty acids are important for maintaining the membranes of all cells and for making prostaglandins which regulate many body processes, including inflammation and blood clotting. High levels of omega-3 fatty acids, for example, are found in oily fish, and are believed to explain the low levels of heart disease observed in populations with fish-rich diets. The fats also enable the lipid-soluble vitamins A, D, E and K to be absorbed from food, and may aid in regulating body cholesterol metabolism.

Linoleic acid is an omega-6 fatty acid. It is biologically inactive before it is catalyzed by the body into other omega-6 fatty acids gamma linoleic acid (GLA), dihomo-gamma linoleic acid (DHGLA) and arachidonic acid (AA). Linoleic acid occurs widely in plant glycerides or fats. Common sources include many vegetable oils such as flax seed, safflower, soybean, peanut, and corn, as well as dairy fats. It is essentially insoluble in water, but soluble in alcohol, ether, oils and fixed alkali hydroxides. Linoleic acid is essential in human nutrition and is used also for soaps, animal feeds, paints, drying protective coatings, emulsifying or smoothing and wetting agents, and in biochemical research. Linoleic acid appears to protect against strokes and to lower blood cholesterol, according to reports by the Journal of the American Heart Association. Other researchers report that linoleic acid may reduce the risk of ischemic stroke by lowering blood pressure and improving circulation in small blood vessels. The conjugated form of linoleic acid or CLA has been associated with health benefits such as lowered risk of cancer and atherosclerosis. Prepared CLA is available as a supplement.

Other useful fatty acids include oleic acids, as well as palmitic ($C_{15}H_{31}COOH$) and steric acids ($C_{17}H_{35}COOH$). Soybean triglycerides contain linoleic and oleic polyunsaturated fats. Fatty acids, such as these, would be useful as or useful in dietary supplements (e.g., fat burners, cholesterol reducers, biochemistry), paints, coatings, emulsifiers, pharmaceuticals, animal feed, soaps, and margarine. It would be desirable to provide new synthetic methods for making fatty acids such as linoleic and oleic polyunsaturated fats.

SUMMARY OF THE INVENTION

Methods, systems, and devices are provided for synthesizing one or more useful chemical products. In one aspect, a method is provided for synthesizing one or more chemical products from a renewable oil, comprising the step of flowing a fluid which comprises a renewable oil through a high voltage electrical field effective to catalyze a chemical reaction involving the renewable oil. Examples of renewable oils include vegetable oils, animal fats, bio-oils, and combinations thereof.

In one embodiment, the fluid further comprises an alcohol mixed with the oil, and the chemical reaction produces biodiesel. For example, the alcohol can include methanol, ethanol, or a combination thereof. In one embodiment, the weight fraction of the alcohol in the mixture of oil and alcohol flowing into the electrical field is between about 4% and about 30%, e.g., between about 12 and about 15%. In one embodiment, the biodiesel is further reacted to produce acetic acid.

In another embodiment, the fluid further comprises a caustic agent and the chemical reaction produces glycerol, surfactant, or both glycerol and surfactant. In one embodiment, the fluid further comprises an alcohol, such as ethanol or isopropyl alcohol, mixed with the caustic agent, such as sodium hydroxide or potassium hydroxide. For example, the fluid can comprises an aqueous solution of caustic agent and alcohol, and the chemical reaction produces glycerol.

In a preferred embodiment, the electric field is applied to the fluid by flowing the fluid between an anode and a cathode of an electro-potential cell, and preferably the electrical potential is between about 2000 and about 8000 volts per inch between the anode and cathode. Preferably, the electric field is generated by a direct current. In one embodiment, the electro-potential cell comprises a housing in which the anode and cathode are secured, said housing having a fluid inlet through which the fluid enters the housing and a fluid outlet through which the fluid is discharged from the housing after passing through the electric field. In one example, the housing is cylindrical in shape, the fluid inlet having a central axis approximately coextensive with the central axis of the fluid outlet. In other examples, the electro-potential cell comprises a T- or L-shape housing in which the anode and cathode are secured, said housing having a fluid inlet through which the fluid enters the housing and a fluid outlet through which the fluid is discharged from the housing after passing through the electric field, the fluid inlet being oriented approximately perpendicular to the fluid outlet.

In another aspect, a chemical processing system is provided that includes (1) a main supply vessel containing a reactant fluid which comprises a renewable oil; (2) a first electro-chemical reactor which comprises a power source and a housing in which an anode and a cathode are secured, said housing having a fluid inlet through which the reactant fluid enters the housing and a fluid outlet through which a product fluid is discharged from the housing after passing through a high voltage electric field generated by the power source between the anode and the cathode; (3) a first product vessel for collecting the product fluid discharged from the housing; and (4) a pump or other means for directing a quantity of the reactant fluid from the supply vessel through the electro-chemical reactor and into the first product vessel. In one embodiment, the system further includes a second electro-chemical reactor in series with the first electro-chemical reactor.

In one embodiment, the system further includes an alcohol supply vessel, which contains an alcohol, and a pump or other means for directing a quantity of the alcohol into a quantity of the reactant fluid, into a quantity of the product fluid, or into both. In a further embodiment, the system comprises a distillation unit and a pump or other means for directing a quantity of the product fluid into the distillation unit. In one embodiment, the renewable oil comprises a vegetable oil, an animal fat, a bio-oil, or a combination thereof, and the product fluid comprises biodiesel. In one embodiment, at least a portion of this biodiesel is mixed with an alcohol and heated to form a mixture of acetic acid and byproducts. The mixture can be distilled to separate the acetic acid from a portion of the byproducts. The distilled acetic acid can be cooled to precipitate the acetic acid, forming glacial acetic acid. The glacial acetic acid can be separated from a second portion of the byproducts by centrifugation.

In another aspect, an improved electro-chemical reactor is provided, which comprises: a housing having a fluid inlet and a fluid outlet, a fluid flow path being defined therebetween; an anode secured within the housing in the fluid flow path; a cathode secured within the housing in the fluid flow path; a direct current power supply in electrical connection to the anode and to the cathode effective to create an electric field between said cathode and said anode; wherein the anode is secured with a holder comprising a ceramic material. In one embodiment, the ceramic material comprises a fused silica oxide. In another embodiment, the anode comprises a beryllium-copper alloy and is in the form of an elongated rod which tapers to a point in the direction of the cathode. In one embodiment, the cathode is in the shape of ring which fittingly engages an inner surface of the housing, said fluid flow path extending through the ring. In one embodiment, the housing is cylindrical in shape, the fluid inlet having a central axis approximately coextensive with the central axis of the fluid outlet. In another embodiment, the reactor comprises a T- or L-shape housing in which the anode and cathode are secured, said housing having a fluid inlet through which the fluid enters the housing and a fluid outlet through which the fluid is discharged from the housing after passing through the electric field, the fluid inlet being oriented approximately perpendicular to the fluid outlet.

In still another aspect, a biodiesel fuel is provided which includes methyl esters derived from a renewable oil; and etherified glycerin derived from the renewable oil, wherein the methyl esters and etherified glycerin, (1,2,3 propanoate), are produced from the renewable oil in an electro-catalyzed process. In preferred embodiments, the fuel further includes a petroleum diesel fuel and lowers $NO_x$ emissions without lowering the heat value of the fuel.

DETAILED DESCRIPTION OF THE INVENTION

Figure 1:
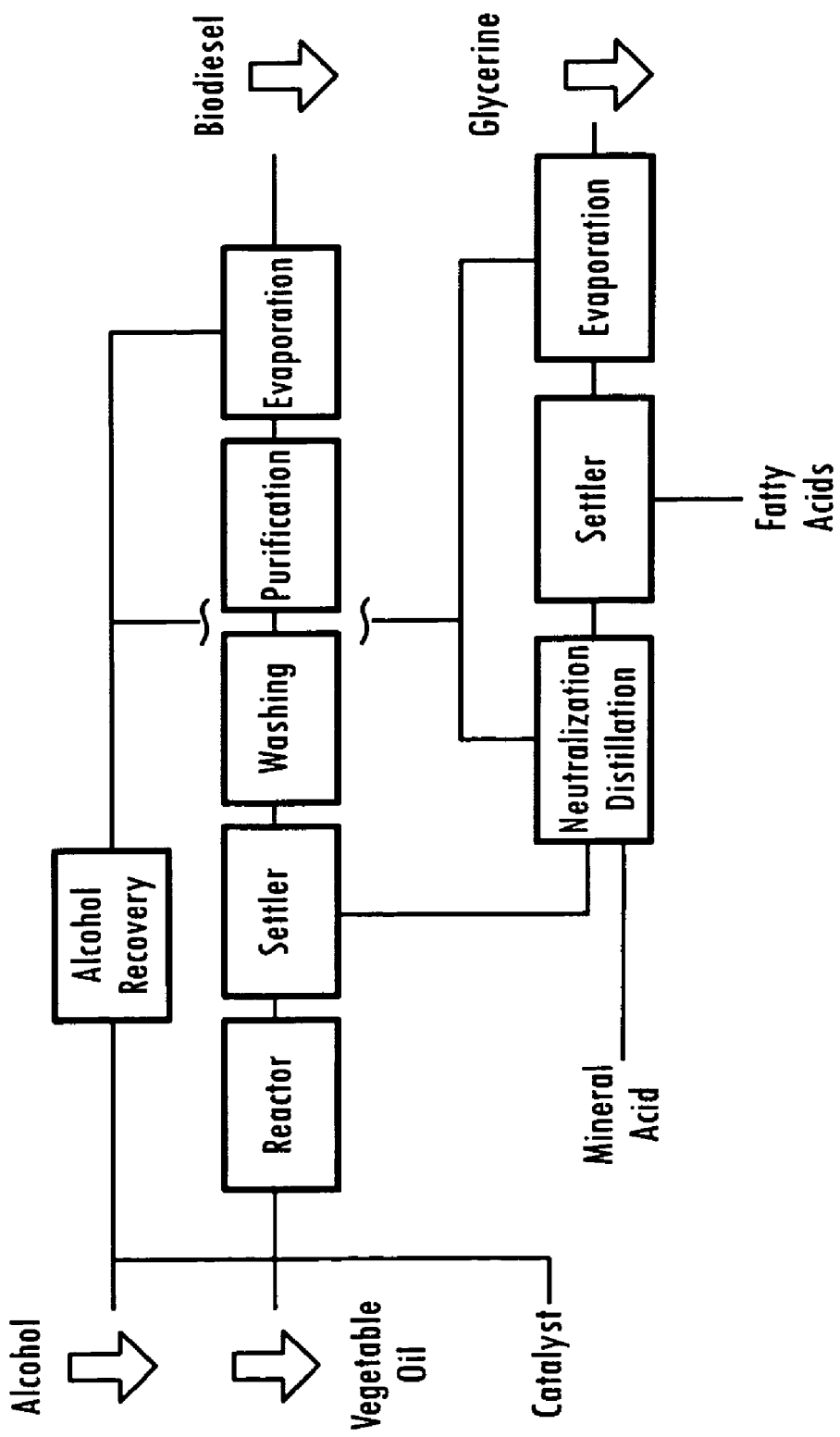
FIG. 1 is a process flow diagram of a prior art process for biodiesel synthesis via transesterification.
Figure 2:
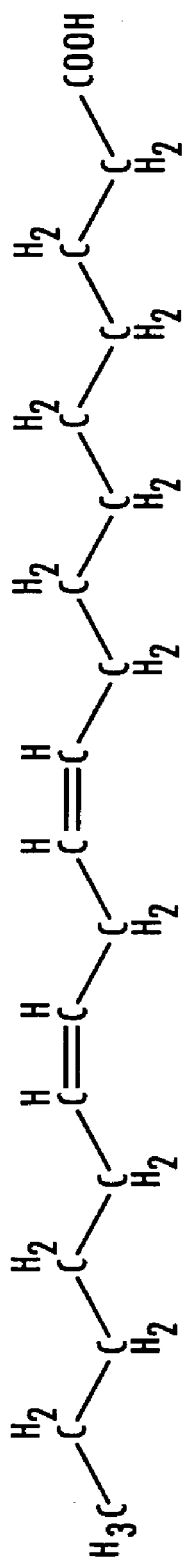
FIG. 2 is a drawing of the chemical structure of linoleic acid.
Figure 3:
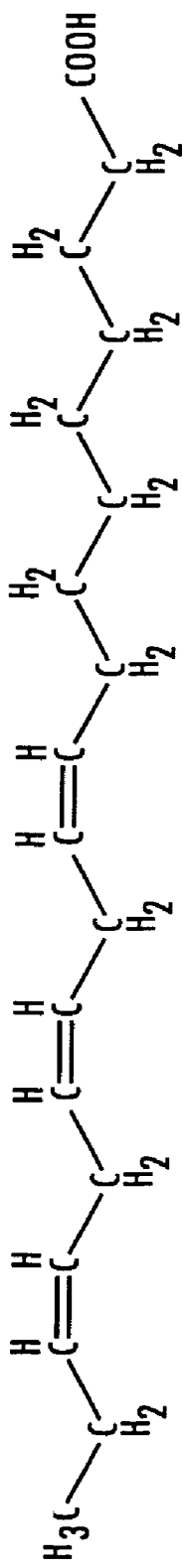
FIG. 3 is a drawing of the chemical structure of alpha linolenic acid.

Devices, systems, and methods have been developed for the synthesis of several valuable chemical products (or intermediates) using a high voltage electric field. It has been discovered that the use of a high voltage electrical field in combination with various chemical components provides an efficient synthesis route. Advantageously, the devices and methods can decrease the cost and time of various chemical reactions by reducing or eliminating the need for additional and costly separation or purification processes. In preferred embodiments, the processing methods are conducted at low or atmospheric pressure, without metallic ion catalysts, and do not utilize petroleum sources or rely on biological fermentation methods.

In preferred embodiments, the methods, systems, and devices are used for the production of biodiesel, surfactant, hydrogen gas, and/or acetic acid, and for polymerization. In one preferred embodiment, the biodiesel, surfactant, acetic acid, and/or glacial acetic acid is made from a renewable oil (e.g., a bio-oil or other non-petroleum-derived oil). For example, the reactant can comprise a crude or refined vegetable oil, animal fat, tall oil, or used cooking grease.

In conventional processes, triglycerides are reacted with alcohol to form biodiesel, and in the process the transesterification reaction occurs where the triglyceride molecule is broken into two components, forming glycerol and esters, and where ester is formed instead of the initial fatty acid. The presence of alcohol and catalyst in the reaction brings 3 hydrogen atoms to the glycerin molecule, increasing hydrogen atoms from 5 to 8. In other words, the present biodiesel production process advantageously uses an electrical charge to catalyze formation of glycerol ether in a single step process while forming esters from the triglyceride molecule. This is a significant process improvement over conventional processes.

Under conventional biodiesel processes, the term for this is "hydration of the glycerin," and it leads to the formation of "glycerol," which is immiscible with ester and separated out of the biodiesel. In contrast, the biodiesel production methods described herein advantageously do not remove the free fats before reaction, but rather retain them, increasing the yield, improving the BTU value, and lowering $NO_x$ emissions. The biodiesel production methods described herein advantageously can use oil sources that are high in free fats, converting them to ester in a single step process, as outlined in FIG. 7. Moreover, the process yield essentially no byproducts, other than hydrogen gas, that need to be removed from the process, thereby improving yield and lowering production costs. In addition, the biodiesel production methods described herein advantageously detaches the glyceridic part from the triglycerides and forms "dehydrated glycerol," and with the addition of excess alcohol etherifies the dehydrated glycerol to form 1,2,3 Proponoate, which effectively functions as a biodiesel "fuel additive" to improve/lower $NO_x$ emissions. Without the presence of traditional catalyst containing OH ions, there is a effectively zero probability of providing the 3 additional hydrogen atoms required to form the traditional 8 hydrogen glycerin molecule form. In working examples, the biodiesel made using the electro-catalytic reactor process described herein was observed to be homogenous and free of any settled glycerin material. Furthermore, formation of the etherified glycerol molecule was found to enhance product quality by improving fuel combustion thermal output and lowering engine $NO_x$ emissions.

In another aspect, the present devices can be used for the sterilization of fluids, liquids, solutions, suspensions, gels, foods, beverages, gases, or other materials that are not detrimentally altered from exposure to a high voltage electrical field.

As used herein, the term "high voltage" refers to a voltage of at least 600 volts.

As used herein, the terms "comprise," "comprising," "include," and "including" are intended to be open, non-limiting terms, unless the contrary is expressly indicated.

The Processing Methods

The present devices and systems are used in various chemical synthesis processes in which one or more fluid chemical reactants are made to flow through a high voltage electric field to catalyze a desired reaction. The processes can be conducted batchwise, or more preferably continuously, or in a combination using some batchwise steps and some continuous steps. In various embodiments, the processes involve synthesizing one or more products or desirable by-products from a renewable oil. In a preferred embodiment, biodiesel is produced, alone or in combination with one or more products selected from surfactants, hydrogen gas, polymers, acetic acid, and glacial acetic acid.

Biodiesel Synthesis

It has been discovered that when an alcohol such as methanol and an oil such as crude vegetable oil/fat come in contact with a strong electric field, the resulting product is methyl ester. The general formula is given below.

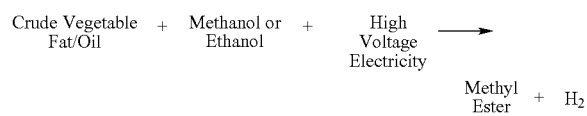

In one embodiment, an oil or oil mixture is pre-heated (e.g., to a temperature from about 25° to about 65° C.) to form a heated oil feedstream. An alcohol feedstream also is preferably preheated (e.g., to about 45° C.), and then the two preheated feed streams are mixed. Alternatively, the oil and alcohol can be mixed together and then the resulting mixture preheated. The mixture is then fed (e.g., pumped) through the electro-chemical reactor, where the reactants are catalytically reacted, preferably at a temperature of about 85° C. In a preferred embodiment, reaction yield is essentially 100% methyl ester and free of side reactions and precludes contaminant separation after reaction for purification purposes.

In certain preferred embodiments, the methanol mix ratio with crude vegetable oil is from about 4% to about 30% or from about 12% to about 15% to produce 100% yield methyl ester with glycerolic ether form, (1,2,3 Propanoate), as a byproduct. Etherified glycerol additive, a highly cationic molecule or (1,2,3 Propanoate) does not precipitate out of solution and is 100% soluble in mono alkyl ester. (1,2,3 Propanoate) is also highly miscible in petroleum diesel fuel.

In a preferred embodiment, the reactor provides an applied voltage from about 2000 to about 8000 Volts. The voltage applied determines the reaction carbon chain length of the methyl ester. Where the starting carbon chain length is between (18-33) and the reaction component carbon chain length is (11-14). Carbon chain length is important in the biodiesel BTU value as compared to petroleum diesel. Biodiesel BTU value is equal to or higher than petroleum diesel. As used herein, the term "biodiesel" refers to a methyl ester-containing composition that is suitable for use as a fuel in a diesel engine.

Advantageously, the biodiesel made by the methods described herein can have a BTU value equal to or greater than that of petroleum diesel or conventional biodiesel. For example, degummed soy bean oil biodiesel has a heat value of 35,605 BTU/liter (134,800 BTU/gallon), whereas pipeline petroleum diesel has a heat value of 34,606 BTU/liter (131,000 BTU/gallon). Based on this comparison, the biodiesel can provide a three percent increase in power over petroleum diesel Furthermore, conventionally made biodiesel BTU values typically range from 30,908 to 31,960 BTU/liter (117,000 to 121,000 BTU/gallon), which translates to an average 9% loss of power compared to pipeline petroleum diesel. Therefore, the biodiesel made by the methods described herein, which contains (1,2,3 Propanoate) can provide an average net power improvement of 12% compared to conventional biodiesel.

In one embodiment, the oil is pumped from a preheat tank and methanol (99.9% pure) is metered into the flow stream and static mixed at about 8% to about 22% ratio by weight. In one embodiment, the ratio is from about 12% to about 15% ratio by weight. In one embodiment, for example, the continuous flow velocity though the reactor is between about 15 and about 20 feet per second, and the reaction goes to completion in approximately 180 milliseconds. In an alternative embodiment, the oil and methanol are premixed batchwise.

A variety of oils and fats can be used. In particular, the methods described herein can provide for conversion of triglycerides and free fats into methyl ester with unique characteristics for converting all types of vegetable oils whether edible or non-edible, animal and poultry fats, tall oils, bio-oils (such as those formed from pyrolysis), waste or used cooking oils for producing biodiesel without detected formation of glycerol and surfactants.

In one embodiment, the systems, devices and methods are used to convert bio-oil to biodiesel without the formation of glycerol and surfactants. An exemplary scheme is shown below.

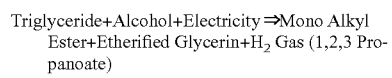

In one embodiment, the biodiesel production method includes application of a DC current or AC charge of at least 1,800 volts. In one embodiment, the DC charge is pulsed from about 2,600 to about 8,000 volts. In another embodiment, the DC charge is a 50% duty cycle 25 millisecond pulse. Other charge pulses and duty cycles that transesterify the oil and alcohol into biodiesel also can be used. In yet another embodiment, the method is a continuous process for formation of methyl ester in which the reaction time is, for example, from about 100 to about 300 milliseconds, from about 80 to about 90 milliseconds, or from about 10 milliseconds to about 2 seconds. In one embodiment, the formation of methyl ester is carried out at atmospheric pressure and a temperature from about 25° to about 85° C. In one embodiment, the reaction temperature is below 45° C.

In a preferred embodiment, the reaction temperature is between about 69 and about 95° C., more preferably between about 75 and about 85° C., and following the reaction, the fluid product discharged from the electro-chemical reactor is held (e.g., in a secondary reaction vessel or storage tank—heated, insulated, and agitated) at a temperature greater than about 61° C. for between about 15 and about 45 minutes to allow the chain reaction to be completed. Stirring of the product is important to liberate trapped hydrogen gas molecules from the fluid.

Surfactant and Glycerol Synthesis

In one embodiment, an electroestrification process for formation of surfactant and glycerol is provided. For example, an electro-saponification process is provided that involves the formation of surfactant and/or glycerol. The general formula is given below.

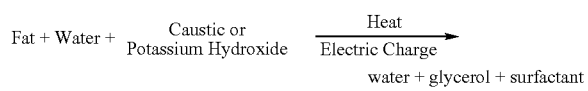

The process is preferably and advantageously performed without a catalyst, solvent, or electrolyte. The resulting product of the reaction provides 100% yield without side reactions typically formed with use of catalyst. In one embodiment, the electrochemical reaction for surfactant reduces formation time by a factor of from about 13,000 to about 16,000. In one embodiment, glycerol is formed at high purity from about 96% to about 99%.

In one embodiment, the process is adapted from conventional processes for manufacturing surfactant, where sodium hydroxide produces solid soap and potassium hydroxide produces liquid soap, and fats (1 mole)+caustic (3 moles, either sodium hydroxide or potassium hydroxide)+batch heating (35 minutes at 90° C.)=surfactant.

In the present case, surfactant can be made directly from methyl ester by adding 1% by weight caustic yielding surfactant and glycerol. While the method can be conducted as a batch process, it advantageously is conducted as a continuous process in which the reactions occur in milliseconds, much faster than with conventional batch processes.

The processes are further described in the examples below.

Acetic Acid Synthesis

In one aspect, acetic acid is made by a process using a high voltage electro-static force to replace traditional catalysis in chemical reactions. This electro-catalytic reaction overcomes significant limitations that exist with traditional methods, and provides chemical reaction efficiency, reaction product purity, and the ability to form reaction products without unwanted side reactions.

Figure 9:
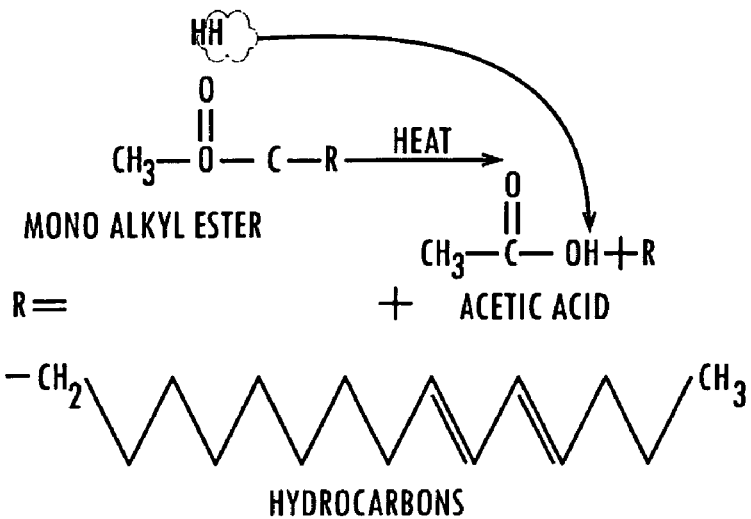
FIG. 9 is a drawing illustrating the chemical structures involved in the chemical reaction of a monoalkyl ester to produce acetic acid and hydrocarbons.

In the process, vegetable oil triglycerides (crude, degummed or refined) are mixed with alcohol (methanol or any type), heated, and then the mixture is passed through the electro-catalytic reactor. Chemical conversion results in a biofuel with a dehydrated glycerol, (1,2,3 Propanoate), and hydrogen gas byproduct. Hydrogen is liberated as a gas from the process while the dehydrated glycerol ($CH_2OCHOCH_2O$) remains as a homogeneous solution. When subjected to heat during distillation (for example, above 300° C. at either atmospheric pressure or vacuum at 400 mm Hg), the reaction product undergoes a reverse reaction. The highly active methyl ester disassociates back into acetic acid and a simple hydrocarbon byproduct. See FIG. 9. Some hydrogen is liberated as a gas. A small amount of water may be formed. When the reaction product is cooled below 25° C., precipitation of glacial acetic acid begins. This glacial form of acetic acid then can be separated using techniques known in the art, such as centrifugation or a tank settling/decantation process. In one embodiment of the process, acetic acid is advantageously formed without using water as a reaction component.

In one embodiment, the acetic acid is made from mono alkyl ester using high temperature distillation, wherein the distillation temperature exceeds 300° C. In one embodiment, the system and method oxidizes mono alkyl ester with an alcohol to form acetic acid with a hydrocarbon residue. Examples of suitable alcohols include methanol, ethanol, isopropanol, and other alcohols. In one embodiment, the system and method provide for the separation of glacial acetic acid by lowering the distillate temperature to below 12° C. and centrifuging the solid precipitate glacial acetic acid from the hydrocarbon residue. The separated hydrocarbon residue then can be used as either as a fuel or solvent.

In one embodiment, the acetic acid is produced as a byproduct of a polymer and biodiesel manufacturing process. For instance, the system provides a method of producing biodiesel fuel, as an intermediate in the production of acetic acid, from renewable sources that is cost competitive with petroleum diesel fuel. In one embodiment, for example, the devices and systems can be used to synthesize biodiesel and ultimately to produce acetic acid.

Polymerization of Esters

In one embodiment, the devices and systems described herein are used to form ester polymers. Polymerization of esters can be achieved using high electro-energy process for treating vegetable oils with an alcohol, as described above. One of skill in the art can select the desired polyester from basic chemistry of ester formation; i.e. selecting the reagents such as alcohol and an acid, and applying the basic chemistry to the present devices and methods. For example, a general ester formation synthesis with the following reagents will achieve the desired ester polymer when used along with the devices and methods herein The reaction process is outlined in FIG. 8, where the polymer solvent is biodiesel, and where solvent reduction to increase resin solids is also contemplated. Advantageously, the process does not require the environmentally hazardous solvent isocyanate and is therefore a more desirable process. In fact, no chemical catalyst is required for the polymerization reaction when using the present systems and methods including an electro-catalytic reactor. Essentially any solvent solids content can be obtained using the process. An exemplary reaction is shown below:

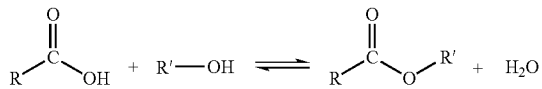 (5)

wherein R and R' are independently alkyl (substituted or un-substituted, branched or straight). When applied to a high voltage electric field, a polyester resin molecule is produced. Although the reaction provides a method with less separation or purification from the prior art, one of ordinary skill in the art may also employ any separation or purification methods known which will not adversely affect the formation of the desired polyester. In various embodiments, the process is adjusted to modify the polymerization of esters to achieve a desired high thermal stability of the polyester resin. For example, different additives or catalysts may be added to achieve the desired products. The conditions may be done at any temperature, atmospheric pressure, or pH that will not adversely affect the formation of the desired polyester.

The Electro-Chemical Reactor Device and Processing Systems

The synthesis processes described herein are carried out in a system that includes an electro-chemical reactor device. The system typically includes additional process equipment to control the flow of reactants and products to and from the reactor.

Figure 6:
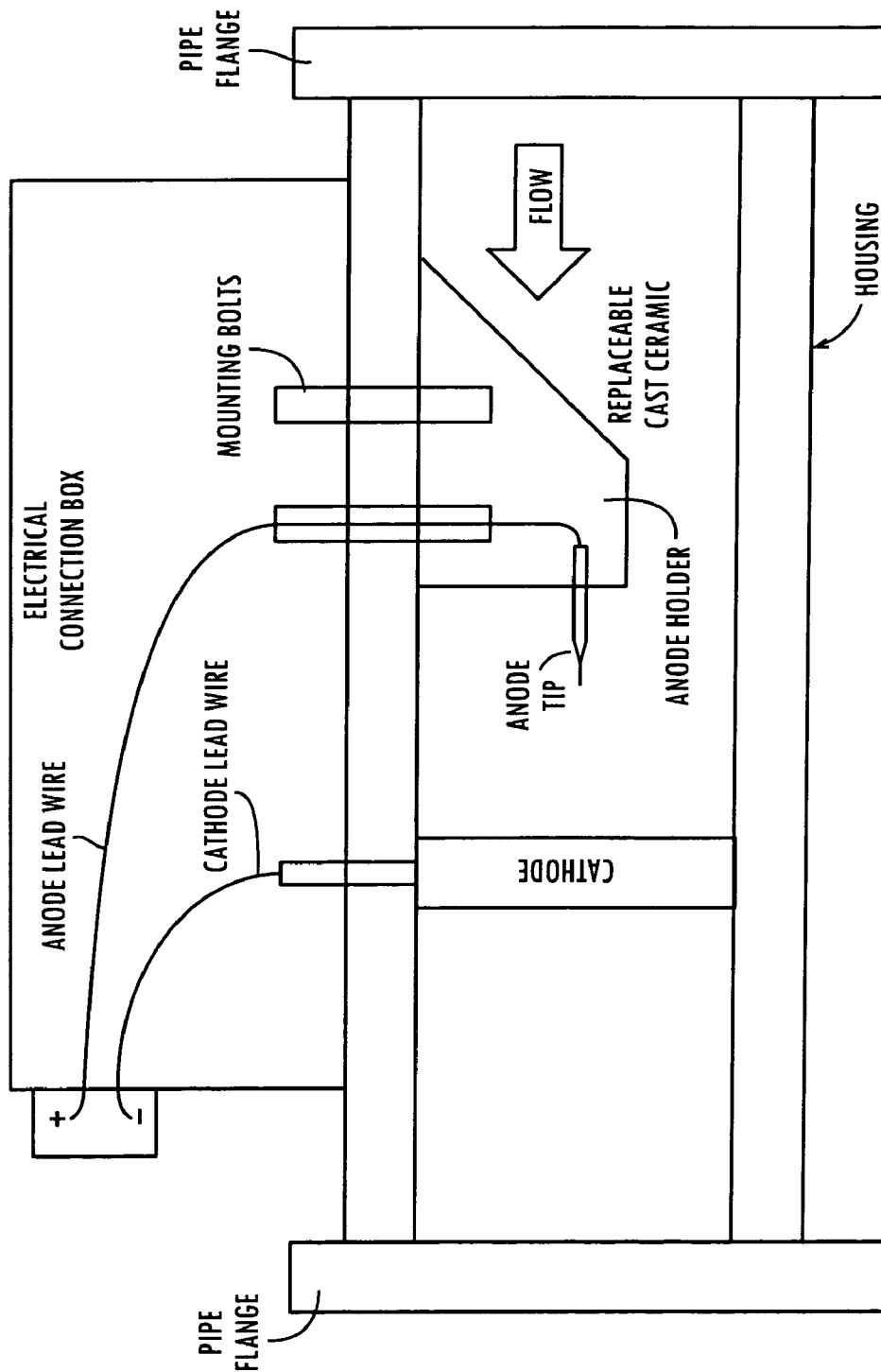
FIG. 6 is a cross-sectional view of one embodiment of a linear electro-potential cell.

The electro-chemical reactor, or electro-potential cell, has been developed to provide a controlled application of a high voltage electric field to a flowing fluid. The reactor comprises a housing containing at least one anode and at least one cathode for applying an electric field to a fluid flowing through the housing. In one embodiment, the electro-chemical reactor is adapted from the devices disclosed in U.S. patent application Publication No. 2002/0121352 A1 by Lawson, et al., which is incorporated herein by reference. One embodiment of the device is illustrated in FIG. 6.

The housing of the reactor has at least one fluid inlet and at least one fluid outlet. It can have a variety of any shapes or configurations. In one embodiment, the housing is cylindrical in shape. In other embodiments, the housing has a cross-sectional shape selected from circular; oval; three-sided, e.g., triangular; four-sided, e.g., square, rectangular, trapezoidal, or parallelogram; five-side, e.g., pentagram; six-sided; or any sided that will allow a controlled application of a high voltage electric field applied to a fluid flowing therein. The housing is configured in any way that allows the fluid to pass through the high voltage electric field. For example, the configuration may be linear, T-, N-, W-, or L-shaped, such that there is a fluid inlet and a fluid outlet. Preferably, the direction of the fluid flow is from the anode to the cathode.

The anode (the positive electrode) may be made of any material that allows the flow of electrons. Representative examples of anode materials include metals, such as copper, silver, gold, magnesium, zinc, aluminum, iron, nickel, tin; non-metals or combinations thereof (e.g., alloys or coated or multi-layered structures), such as carbon-based materials such as graphite; or combinations of metals and non-metal. The metals can be galvanized or formed in combination with oxygen or oxides. In a preferred embodiment, the anode is made of a copper alloy.

The cathode (the negative electrode) may be made of any material to which positively charged ions migrate when an electric current is passed. In a preferred embodiment, the cathode is made of a copper alloy. In other embodiments, the cathode comprises a stainless steel, platinum, nickel, or iron, or alloy thereof. In a preferred embodiment, the cathode is in the form of a band of material that is circumferentially attached to an interior surface of the housing.

The electric field is a high voltage field, which may be generated from essentially any source known in the art. The electric field may be generated from a direct current (DC) or alternating current (AC). In preferred embodiments, a direct current electric field is more desirable. Preferably, the voltage created between the anode and the cathode is one that does not adversely affect the target product. In various embodiments, the voltage ranges from about 800 to about 8000 volts per inch between the anode and cathode. Typically, the higher the voltage used, the shorter the carbon chain that results. Greater voltages can cause excessive ionization at the anode, which significantly increases current consumption and consumption rate of the anode material. Biological activity is effectively neutralized by application of voltages above 800 (8.5 volts/mm). While not be bound to any particular theory, it is believed that such voltages coagulate cell plasma or causes cell lysis, halting life in the biological organism. A life form is incapable of restoring the plasma after coagulation.

Power consumed is directly proportional to anode surface area. The geometric relationship of anode discharge surface area (current density) is proportional to power consumed. To minimize power, the anode must also be minimized. The cathode surface area can be large compared to the anode surface area. To treat 100% of the fluid flow, one electrode must encompass the entire flow, or be of sufficient size or surface area. The minimal surface area is the internal circumference of the pipe wall.

Under these circumstances, if alternating current is employed, when the larger cathode surface becomes the anode, the surface coats over or insulates with ionic material.

The geometric relationship between the cathode and the anode is important to both power consumption and low-maintenance-free operation of the electro-potential cell. Preferably, the high-voltage, low power electro-potential cell provides a minimum anode surface area to reduce power consumption, by orienting the anode towards the cathode such that the anode is tapered in the direction of the cathode, by terminating the anode in a sharp point to reduce power consumption and reduce insulating build-up, and by orienting the anode discharge surface area at approximately 90 degrees to 10 degrees with respect to the cathode surface. The design of the electro-potential cell preferably provides a discharge surface area of the anode which is approximately perpendicular to the cathode surface, and an anode that comprises an elongated rod which tapers to a point in the direction of the cathode.

The distance of between the anode tip and the cathode also is important to both power consumption and low-maintenance-free operation of the electro-potential cell. The distance between the anode and cathode varies in relation to the diameter of the housing unit. For example, the as the diameter of the housing unit increases, the distant between the anode tip and the cathode may also increase. Other conditions that can affect the distance between the anode tip and cathode include the conductivity of the particular materials used for construction of the electrodes. For example, if the metals used for the anode and cathode have a high conductivity value, then the distance between the anode tip and cathode may decrease. The preferred distance between the anode and cathode is any distance that optimizes power consumption while achieving the desired chemical synthesis, e.g., polymerization of polyester, production of biodiesel, sterilization, or other reaction. Distance is not limited and varies in relation to the flow elements cross sectional distance. Anode to cathode distance generally increases with larger flow element cross sectional distance.

Fluid flow velocity can be critical, in that it should provide enough time and thus exposure within the electric field for the reaction to occur. In one embodiment, the process system includes two or more electro-chemical reactors, operating in parallel or in series.

Part of the anode is housed in any material which will stabilize and fix the anode in one place without being materially altered from the high voltage electric field. Representative examples include flexible ceramics; machinable ceramics, castable ceramics, ceramic adhesives; sealants; hi temperature epoxies and putties. In one embodiment, the ceramic anode housing material is made from a commercially available high temperature material, such as supplied by Cotronics Corporation (Brooklyn, N.Y.).

In preferred embodiments, the anode and cathode holder are designed to be a readily replaceable part of the electrochemical reactor. The housing optionally includes at least one access point for periodic cleaning and inspection of the anode, cathode, and their holders. The anode and the anode holder may be removed, replaced or repaired as necessary. For example, where the anode may be a wear item, the anode may be assembled or disassembled with the anode holder for replacement or repair. The anode and anode holder may for example be assembled with a bolt in unit. The cathode and cathode holder may also be optionally removed, replaced or repaired as necessary.

In preferred embodiments, the process system includes insulating piping at the inlets and outlets of the reactor, in order to maintain good power supply voltage control at 600 to 10,000 volts output. For example, long (e.g., 8-foot) sections of non-conductive pipe can be secured to the inlet and the discharge of the reactor to separate it from typical metallic pipe sections. Representative examples of non-conductive pipe materials include PVC, CPVC, fiberglass, and like materials, specified for the particular process, including temperature and corrosion resistance, mechanical strength, and pressure ratings.

Reactants

The systems, methods, and devices described herein require flow of one or more reactants through the electrochemical cell, that is, the reactor. Accordingly, the reactants are in a fluid form. That is, a fluid flows through the reactor, and the fluid comprises the reactants. As used herein, the term "fluid" refers to and includes liquids, suspensions, gels, emulsions, and solutions that have a viscosity value lower that 10,000 Pascal second (Pa s) at room temperature (e.g., at 20° C.). The reactant can be a fluid or it can be a non-fluid dispersed/suspended in a fluid, so long as the combination is a fluid. In one embodiment, the process fluid conductivity is from about 0.10 to about 1,900 mmhos. In yet another embodiment, the process fluid conductivity is from about 100 to about 1700 mmhos. In yet another embodiment, the process fluid conductivity is from about 500 to about 1200 mmhos.

Representative examples of fluids include organic and inorganic liquids, oils, and combinations thereof. In a preferred embodiment, the reactant comprises a "renewable oil." As used herein, the term "renewable oil" refers to oils not derived from coal, petroleum, or natural gas. As used herein, the term "oil" refers to and includes vegetable oils, bio-oils, animal fats, and grease. The oil may be edible or non-edible. IT can be natural, crude, refined, or some combination thereof. In a preferred embodiment, the oil is one derived from plants (including natural, hybrid, or transgenic plants).

Examples of vegetable oils include corn oil, canola oil, palm oil, sunflower oil, flax seed oil, safflower oil, tall oil, pine tree tall oil, hydrogenated oil, artificially hydrogenated oil, coconut oil, cottonseed oil, olive oil, palm kernel oil, peanut oil, soybean oil, linseed oil, tung oil, rapeseed oil, sesame oil, babassu oil, perilla oil, oiticica oil, castor oil, Chinese tallow tree oil, Physic nut oil, Cuphea seed oil, oil extracted from algae or micro-algae, oil derived from fruit, and hemp oil. Other oils include bacterial oil, fungal oil, animal oil or grease, such as beef tallow, chicken fat oil, lard, fish oils, menhaden oil, waste grease, soapstock, recycled rendered feedstock oils, and rendered oil or grease generated during the refining of feedstock oils. In other embodiments, the oil is any other products that comprises a glyceride and/or a free fatty acid. The oil can be refined or crude oil stocks. The oil may also be brown grease.

As used herein the term "bio-oil" is an oil derived from the thermal decomposition (pyrolysis) of wood, grasses, or any other cellulose containing woody or non-woody plants. After heating the wood, the smoke is captured and then cooled to produce a liquid fraction containing the bio-oil. Bio-oil has approximately half the energy equivalent of diesel fuel and therefore has many potential applications for industry. Bio-oil may contain both alcohol and the acid needed to be converted to an ester without adding alcohol such as in the case of vegetable oils. Alternatively, alcohol or fatty acid can be added to the bio-oil in the formation of the ester. The present methods and systems can be used to convert bio-oil into an ester upon exposure to the high voltage electric field.

The oil can be one that is commercially available, or it can be obtain by other available means. Examples of oil sources include recycled oils and grease, used cooking oils, virgin vegetable oil, and by products of the Kraft process for papermaking.

In one embodiment, the reactants include an alcohol. As used herein, "alcohol" includes any species with a hydroxyl component. The alcohol may be saturated or unsaturated, substituted or unsubstituted, branched or linear. Representative examples include methanol, ethanol, propanol, iso-propanol, butanol, tert-butanol, pentanol, hexanol, heptanol, octanol, nonanol, and decanol. Methanol and ethanol are preferred.

The devices, systems, and methods described above will be further understood with reference to the following non-limiting examples.

Example 1

Electro-Chemical Reactor

The electro-potential cell is composed of an anode electrode inserted inside a annular (open circular) member, in a housing, through which a reaction mixture is continuously pumped at flow rates of 25 to 200 gallons per minute (95 to 760 liters per minute). The cathode is composed of a soft copper alloy connected to the power supply+(plus) terminal. The anode is held in place by a ceramic holder and has dimensions exposed to the process fluid of ⅛ to 3/16" (3.2 to 4.8 mm) in diameter and ⅝" (15.9 mm) in length. The anode is secured in the center of the fluid flow path by the ceramic holder. The cathode is in the shape of a ring and is inserted inside the circular flow member opposite the anode by a distance of 3.5 inches (89 mm). The cathode is connected to the power supply−(minus) terminal and completes the electrical circuit when fluid flows through the cell. The catalytic reaction occurs when the reaction materials are located in the 3.5" (89 mm) region between the anode and cathode, where the power supply provides either the source of or accepts electrons from the reaction mixture to drive the electrochemical reaction. The initial reaction reaches completion in approximately (80-180) milliseconds. Flow velocity is critical to allow enough time for reaction. If the flow velocity were to exceed the minimum reaction time of 80 milliseconds, an incomplete reaction will occur. Lower flow velocities that exceed the 180-millisecond reaction time have no adverse consequence on the reaction.

The reactor operates with an electrical potential between about 800 and about 5,000 volts between the anode and cathode (8.5 and 52.5 volts/mm), preferably for economical operation, between about 1,000 and about 2,000 volts (10 and 21 volts/mm), and more preferably between about 1,400 and about 1,700 volts (15 and 18 volts/mm).

Figure 4:
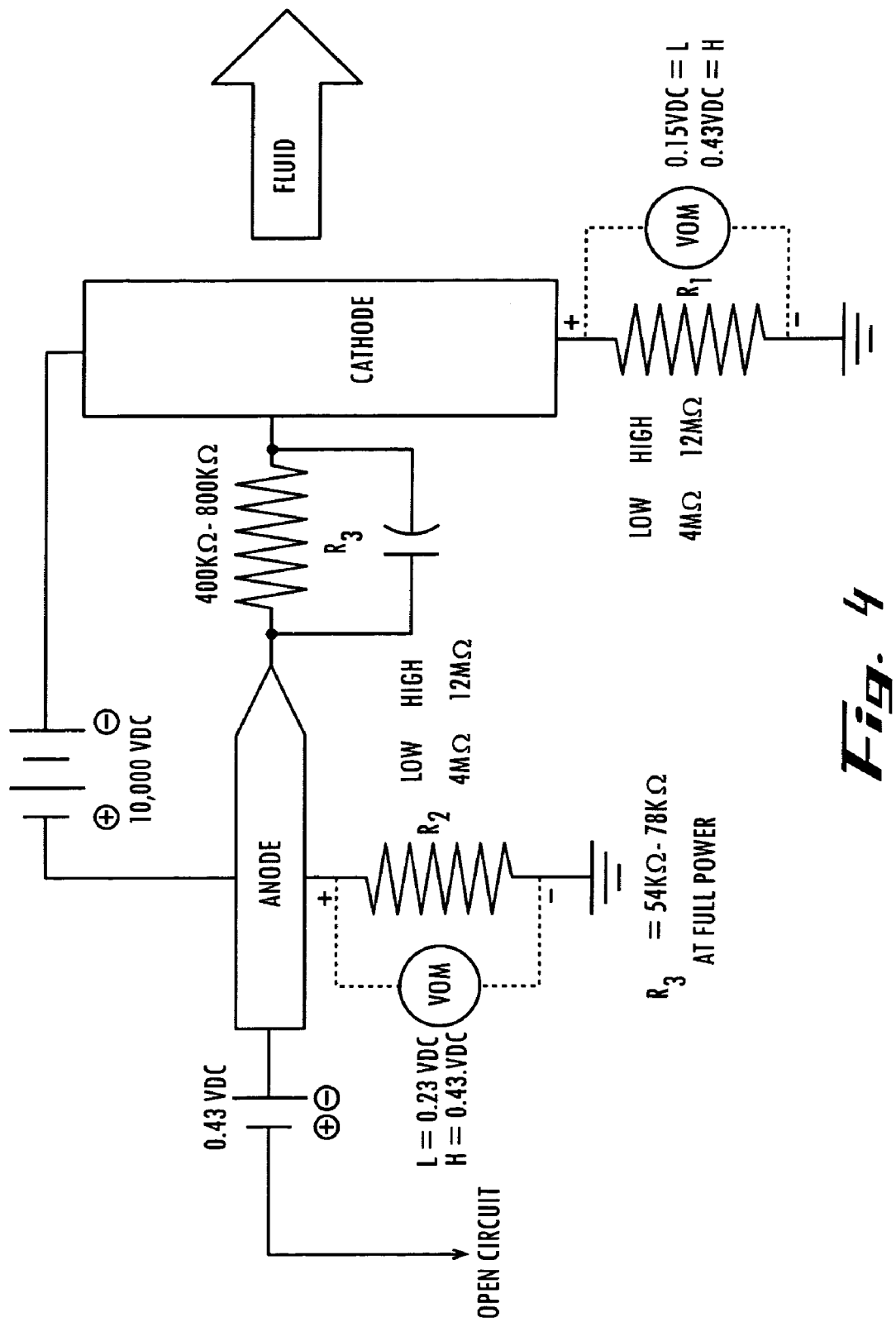
FIG. 4 is an electrical schematic showing one embodiment of a circuit analysis of the electro-potential cell described herein.

A circuit analysis shown in FIG. 4 was conducted to determine the proper electrode isolation from metal conductive pipe sections commonly found in plant/industrial environments. Process fluids flowing through the system at 10 feet per second when measurements were taken contained various compositions of dissolved metallic solids and salts such as sodium hydroxide and others. Anode and cathode resistance was measured at critical points. It was found that galvanic forces contribute significant currents that pass through both electrodes to ground. These ground loop currents originate from various sources in plant industrial pipe and steel support structures and use water and process fluids as a conductive path to ground. The EP Cell electrodes were found to provide low resistance paths to discharge galvanic currents to ground. The EP Cell electrodes normally have approximately 0.45 volts DC to ground. It was found that power supply control circuitry also becomes saturated with these galvanic loop currents and cause voltage control problems on a regulated high voltage power supply. As voltage output increases to each electrode, galvanic currents to ground reference also increase and cause control problems especially above 600 volts DC. Measurements are approximately 0.43 volts drain across ground paths for each Electro-Potential Cell (EP Cell) electrode, where R3 is an important resistance to control for good EP Cell performance (FIG. 4). With the power supply in the off state, R3 resistance was measured between 400 and 800 k-ohms, where this value is ideal for good EP Cell performance. As power supply voltage increases, R3 resistance decreases to approximately 54 to 78 K-ohms. If R3 resistance decreases below 25,000 K-ohms when power supply output voltage reaches 6,000 volts DC, current loading will be at approximately 250 milliamps. If loading exceeds power supply full load capability, voltage control stability will be lost. R3 is controlled by maintaining shield gases and small air bubbles in close proximity (approximately 0.01 mm to 25 mm) to the anode surface during high voltage (600 and above) operation. Gas trapped in the anode holder backwash holds enough gas bubble quantities to keep resistance R3 above 25,000 ohms and allows maximum applied voltage under stable conditions. The value of R3 directly determines the maximum applied voltage.

Figure 5:
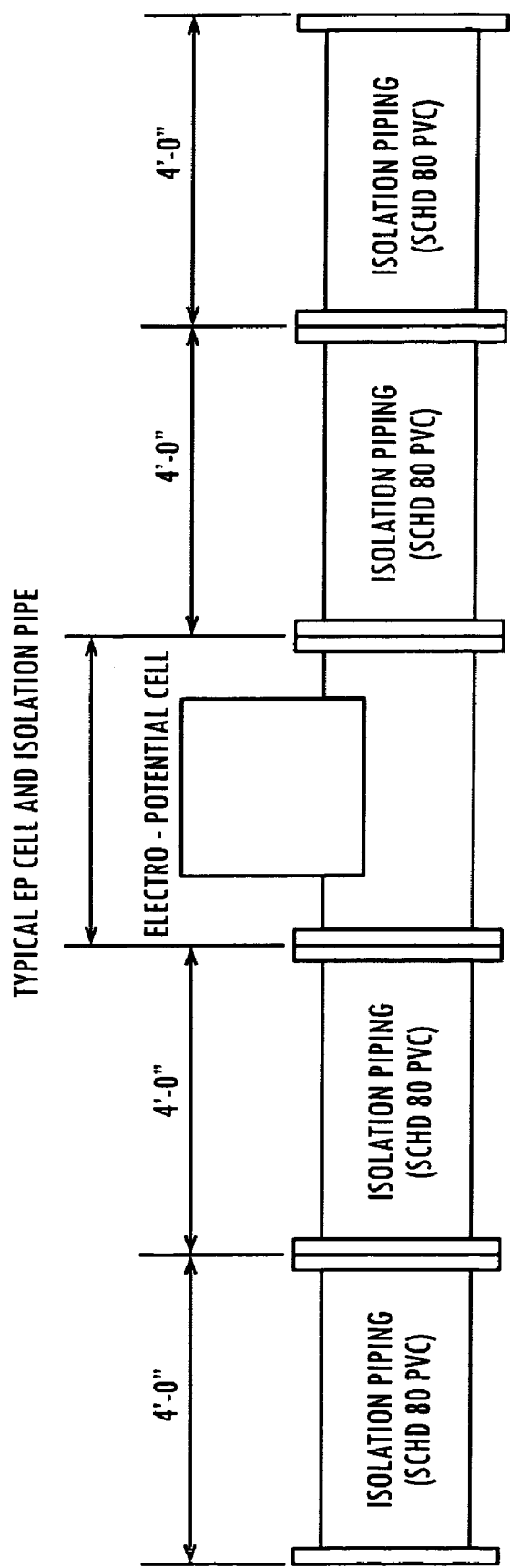
FIG. 5 is a side view of one embodiment of the electro-potential cell installed between electrically isolating piping.

It was found that to maintain good power supply voltage control above 600 to 10,000 volts output, an 8-foot section of non-conductive pipe should be placed on each side of the EP Cell to separate it from conductive metallic pipe sections. FIG. 5 illustrates specific locations of each element of a preferred EP Cell with installed isolation pipe sections. Isolation pipe sections are composed of two individual 4-foot sections of pipe on each side of the EP Cell.

EP Cell and Isolation Pipe sections wall thickness must be considered for calculating safe applied voltage to the electrodes. Conductive fluids will place potentially lethal voltages on the outside surface of the EP Cell and isolation pipe sections. For example, schedule 80 PVC pipe (12.7 mm wall thickness) will have an 800 volt per 3.175 mm withstand capability. A PVC schedule 80 pipe can safely handle up to 3,200 volts DC. Voltages over 3,200 volts could potentially be lethal if a person came in contact with the pipe wall. To ensure adequate safety, grounded metal shields are placed over the entire EP Cell plastic components handling conductive and non-conductive fluids. FIGS. 5 and 6 depict the equipment with partially removed safety shields.

Ideal resistance for good isolation of an EP Cell from ground sources is measured to be approximately 12 meg-ohms. Ideally, isolation of R1 and R2 is in this range (FIG. 4). Fluid flow direction is critical for maintaining R3 resistance. EP Cell orientation can be either horizontal or vertical. Horizontal orientation requires flow to pass across the anode then to the cathode. Reverse flow from cathode to anode typically will not work for voltages greater than about 500 to 1,000 volts with conductive fluids because the anode gas shield and high resistance air bubbles are washed away from close proximity to the anode surface. Resistance of a horizontal EP Cell R3 with reverse fluid flow, cathode to anode, results in values below 2,500 ohms and power supply control stability greater than 500 to 1,000 volts is lost. EP Cell vertical orientation requires flow to be top to bottom and the electrode orientation to be anode top and cathode bottom. This orientation will trap gas and air bubbles on the anode holder backwash, maintaining R3 above 25,000 ohms for a power supply having a 250 milliamp maximum full load current. Other suitable values for R3 are specifically determined by the power supplies maximum output current. Higher output current capability can operate with lower R3 values.

In one embodiment, the distance from the electrical lead wire to the process fluids is from about 2.0 mm to about 300 mm. In another embodiment, the distance from the electrical lead wire to the process fluids is from about 20 mm to about 100 mm. In yet another embodiment, the distance from the electrical lead wire to the process fluids is from about 40 mm to about 51 mm. In one embodiment, the lead wire to the anode is joined via mechanical crimp.

In one embodiment, the anode holder is a replaceable unit that can be removed for scheduled maintenance on a periodic basis. See FIG. 6. It can be constructed of completely machined components using various thermoplastic or polymer substances such as PVC, CPVC, and Krylon. It can include ceramic materials for wear and temperature resistance on the anode holder faceplate. Different interactions were discovered while processing different fluid materials containing varying elements and quantities of dissolved solids and salts commonly encountered with industrial and plant process fluids. Most reactions with heat on the anode holder face surface were destructive to both polymers and ceramics.

Polymer materials were first selected to maintain a tight liquid fit between the anode and holder block to reduce anode seal complexity with holder faceplate. One of these in particular was silicon rubber, which was selected for its high dielectric strength and temperature resistance. Anode holder faceplates constructed of polymer based products including high temperature Krylon. Temperatures of 241° C. were found to cause build up of a conductive material over the face near the electrode about 1" in diameter, which decreased R3 values below the lower threshold of 2,500 ohms and power supply control stability over 500-1,000 volts was lost. Failure of the anode holder material starts with a very light surface coating and continues to build deposits. It becomes more conductive with time, lowering R3 values and resulting in loss of power supply control stability.

In another embodiment, the material of construction has a dielectric strength of at least 3,200 V/12.7 mm; volume resistance of at least 10 to $9^{th}$ power; heat resistance limits of at least 1517° C.; thermal shock resistance.

In one embodiment, the anode materials of construction is a beryllium copper alloy, wherein the anode surface area (current discharge area) is 15.92 mm×4.72 mm in diameter, the anode hardness and temperature rating is at least 307° C., and the compressive strength of the anode holder block is at least 1760 kg/m³.

The thermal heat transfer may range from about 3 to about 4 BTU-°m/hr-ft²° F. In yet another embodiment, the cast materials should have low shrinkage on set-up, for example less than 1%. The holder block should have the ability to resist moisture and thermal shock. In another embodiment, the holder block may be coated, for example with an epoxy resin. In one embodiment, the holder block may be made of any material with low oxidizing and low reducing sensitivity with various chemical attacks.

A castable ceramic material was selected to help solve anode seal problems with sufficient temperature ratings to meet conditions. The material selected was a fused silica, supplied by Cotronics Corp., called Rescor Cer-Cast Ceramic (750), which is a thermal shock resistant, high temperature (1517° C.) rated cast ceramic material. It has high dielectric strength with high compressive compound that is thermally cured under the maximum temperature rating of the anode material. The anode material is beryllium-copper alloy having extremely high hardness for erosion at high temperature. Ceramic cure temperatures are kept below the annealing temperature of the anode copper alloy, meeting RWMA Class 4 specifications of 85,000 psi (5,976 kgf/cm²) tensile and 140,000 psi (9,843 kgf/cm²) ultimate tensile strength properties. Copper alloys were selected for conductivity and minimizing galvanic corrosion properties of compressive lead connection to copper wire to maintain long term low resistance electrical connection.

The entire anode holder is cast with the lead wire and mounting bolts inserted prior to casting. An open pour mold is constructed using PVC with a bolt-together form for easy removal after casting. After casting and 24 hour set-up, the cast part is removed from the mold and heat treated in steps to 226° C. for 12 hours. Heat treatment steps were carried out by slowly increasing the temperature over the 12-hour period from 87 to 226° C. The heat treatment eliminates any unreacted moisture remaining after the set-up process, increasing the dielectric strength. After a slow cool down process, reversing the initial step heating process to bring the anode holder back to room temperature, the cooled holder is sealed with Duralco epoxy (4461), which also was supplied by Cotronics. Duralco is a high dielectric strength epoxy to provide extra moisture seal, and has 307° C. temperature range and high dielectric strength (450 volts per 0.025 mm). The entire block is double coated except for the immediate approximately 51 cm square anode face area. High temperatures at the face will exceed 307° C. and would burn the epoxy possibly leaving a high conductive coating.

It was discovered that operating temperatures of the anode under high voltage can exceed 1627° C. Electron flow into the anode results in a powerful oxidizing environment. Heat build-up is rapid and may fluctuate depending on the availability of reaction components at the anode. The anode and ceramic face may operate as a catalysis environment to further enhance chemical reactions in the immediate vicinity.

One method of constructing the anode holder uses a machined ceramic faceplate with a ceramic shield over the electrode. The 25 mm diameter cylindrical shield covered all but 2 mm of the anode tip. The concept was to keep gases closely associated to the anode surface and increase R3 to maximum and stabilize the trapped gases, allowing higher voltages to be applied to the process fluid. An open face is one example for constructing an anode holder, to prevent high temperatures increases close to the anode holder face block. The process flow helps carry heat away from the immediate anode area helping extend the anodes service life.

It has been observed under conductive fluid flow conditions, there are occasionally spikes in current flow out of the anode. These initially occur infrequently. The current jumps to power supply maximum of 650 ma and then instantly returns to normal ~250 ma at 3,000 volts DC. While not wishing to be bound by any theory, it is believed to result from a small explosion of gases around the anode, driving away the gases and water surrounds the anode causing current to increase. Water is quickly formed back into gases and the current decreases after the anode is shielded in gas. When the explosion occurs, heat is swept away from the face block but quickly returns. This reoccurring thermal shock has a negative affect on low thermal transfer ceramics and damages the ceramic face. It is also believed that as heat builds on the ceramic face due to low thermal transfer, higher temperatures over time increase the severity of the gas explosion setting up the conditions where all of the gas is expelled from around the anode area.

Flow direction is an important process design element. For EP Cells having a diameter greater than 76 mm, preferably between 76 and 760 mm, a linear cylinder is quite effective. Flow through this style element situated horizontally is almost always from the anode to the cathode. If the EP Cell is vertically orientated, then flow should be directed downward with the anode situated above the cathode. This vertical orientation traps air and gas bubbles behind the backwash of the anode holder and keeps R3 above 2,500 ohms with conductive process fluids.

EP Cells having a diameter less than about 76 mm, the EP Cells are formed in a "T" fitting, vertically oriented. See FIG. 7. In one embodiment, the "T" fitting is composed entirely of a thermoplastic material, which is insulated with an outer shell also constructed of a thermoplastic or metal for safety reasons. The electrode enters the cell from the top orientation and flow enters the bottom and is directed upward toward the anode. This flow pattern causes flow to pass over the cathode before the anode. Air and gas bubbles are trapped in the cavity where the anode enters the "T". These small EP Cells (less than 76 mm) use the trapped air around the anode to help insulate the anode seal against the same high temperatures as horizontal units with diameters greater than 76 mm. EP Cells 76 mm and smaller also preferably maintain an R3 (FIG. 4) greater than 2,500 ohms. Any sealing agent suitable in maintaining good voltage insulation characteristics may be used.

Example 2

Saponification Surfactant Formation

In the manufacture of soap, one mole of tallow or vegetable oil is heated at 60-65° C. with 3 moles of sodium hydroxide or potassium hydroxide solution. The heated reaction mixture is pumped through the electro-chemical reactor, wherein a voltage of between 800 to 1500 volts DC (at 190-300 milliamps) is applied through the electrodes to assist the reaction. Complete reaction occurs in (100-190 milliseconds). The reaction time is shortened by an average factor of 14,000. The reaction is fat+water+sodium hydroxide or potassium hydroxide+ heat+electric charge=water+[glycerol intermediate]+surfactant. The present process applied to saponification surfactant formation yields surfactant without the need to remove glycerol. The glycerol intermediate may be driven out with excess water or any method known in the art. This process changes the standard surfactant process from a batch heating to continuous process. The saponification process reaction time is reduced due to the strong anode and cathode electrode potential and their efficient electron exchange function to assist chemical formations and is referred to herein as "electro-saponification." Solid surfactants (soap) obtained from the electro-saponification reaction process does not require sodium chloride addition after boiling the reaction process to obtain high purity. The reactive process materials contain very low un-reacted components and do not require final precipitation with sodium chloride, (salt) to purify the soap after reaction.

In another process, glycerol is formed as the main product instead of a side reaction from saponification. A glycerol product can be obtained directly as a reaction from an aqueous solution of 50:50 caustic/alcohol (ethanol or isopropyl alcohol) and fats. The mixture is heated to (45-65° C.) before passing through the reactor at 2-25 feet per second. The reaction is fat+50:50 caustic/alcohol (ethanol or isopropyl alcohol)+water+electrical charge=water+glycerol, wherein the components are reacted using an applied DC voltage of about 800 to about 1,500 volts. After that reaction, water is added and the glycerol precipitates out of solution at 100% purity. This product is an electro-chemical form of glycerol and is 100% pure.

Example 3

EP Cell Performance and Biodeisel

Oils have a low electrical conductivity and increase R3 above (400-800) k-Ohms. Lower anode current discharge decreases thermal stresses of the anode holder and improve the EP Cell long-term wear and maintenance. It is therefore possible to increase the catalytic voltage operating on the oil to produce better results that conventional catalysis. Where carbon chain length and assisting relocating double bond positions and carbonyl groups along the chain to more suitable locations for better biodiesel performance. BTU output from the converted oil will increase due to high energy content.

High catalytic voltage produced biodiesel has shown to alter the chemical bond structure of the methyl ester. The unsaturated molecule double bonds and locations identified as possible contributors of biodiesel instability have been altered in such a way, resulting in a more stable compound and significantly reducing the amount of oxidation. Biodiesel long-term storage stability and molecule oxidation are important issues for all users. Molecule stability under distillation conditions are represented in Table 1.

TABLE 1

Biodiesel Formulated For High Storage Stability
Vacuum distillation using ASTM Spec. D-1160

| Vacuum Distillation ° C. @ 760 Hg. | Thermal Conditions ° C. |
|---|---|
| 5% | 378 |
| 10% | 398 |
| 20% | 448 |
| 30% | 474 |
| 40% | 487 |

TABLE 1-continued

Biodiesel Formulated For High Storage Stability
Vacuum distillation using ASTM Spec. D-1160

| Vacuum Distillation ° C. @ 760 Hg. | Thermal Conditions ° C. |
|---|---|
| 50% | 532 |
| 60% | 576 |
| 70% | 576 |
| 80% | 576 |
| 90% | 576 |
| 100% | 576 |
| Rec % | 60 |
| Res % | 40 |
| Loss | N/A |

As can be seen from the table, distillation of the product shows the high stability under extreme thermal conditions to 576° C.

Example 4

Polymerization of Esters

The polymerization of esters can be achieved using the electro-potential cell for treating an oil with an alcohol with an electric field. One skilled in the art can modify the polymerization of esters to achieve the desired polyester. For example, different additives or catalysts may be added to achieve the desired products, and particular reagents such as alcohol and an acid can be selected for use with the present devices and methods. The conditions may be done at any temperature, atmospheric pressure, or pH which will not adversely affect the formation of the desired polyester. For example, a general ester formation synthesis with the following reagents will achieve a desired ester polymer:

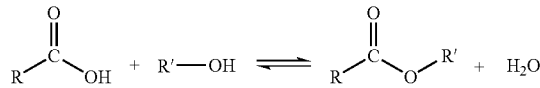

wherein R and R' are independently alkyl (substituted or un-substituted, branched or straight), when applied to a high voltage electric field of the present devices and systems will yield a polyester.

The polymerization process was tested. A resin was produced and preliminary tests on the resin show improved elongation and flexibility at temperature ranges from −16° C. to room temperature. High temperature performance greatly exceeds all other products and was stable at temperatures to 750° C. without de-polymerization. The resin was exposed to high pH conditions at 90° C. without any degradation. It is biodegradable, recyclable and will not harm the environment as conventional polyester polymer processes.

Example 5

Sterilization

Fluids that are not materially altered by exposure to a high voltage electrical field may be sterilized using the devices and methods provided. The temperature and pressure range used to sterilize fluids, liquids, solutions, suspensions, gels, foods, beverages, or gases are carried out at any temperature or pressure that will not vaporize or adversely alter the physical or chemical properties of the products, for example, which will not destroy or decrease the nutrient values of the food or beverage (e.g., fruit juice). Unlike conventional sterilization methods which uses heat above 175° F. to destroy or denature the microorganisms, the fluids may be sterilized at a temperature below 175° F. with the devices and methods provided; thus, will not destroy or decrease the nutritional, therapeutic, or cosmetic value of the fluids, liquids, solutions, suspensions, gels, foods, beverages, or cosmetics.

The flow rate and quantity of the fluids, liquids, solutions, suspensions, gels, foods, or gases may be at any rate which will which decrease the kill or decrease the formation of bacteria, fungi, parasites, viruses, or other microorganisms associated with adverse reactions upon use or consumption by humans or other mammals.

Example 6

Variable Acetic Acid Process Controls

Figure 8:
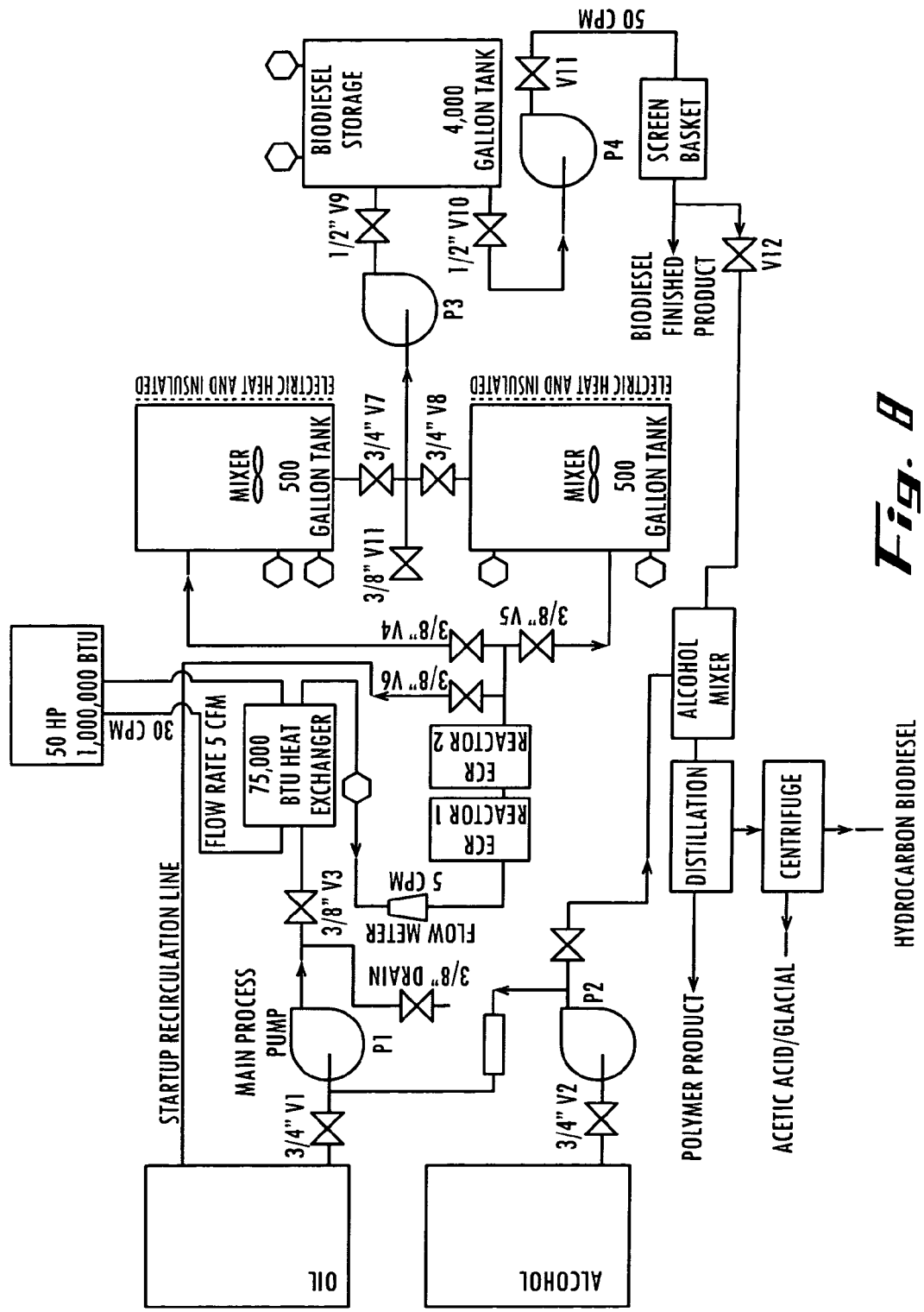
FIG. 8 is a process flow diagram of one embodiment of a process for converting bio-oils into biodiesel, polymers, acetic acid, and glacial acetic acid.

In one process, shown in FIG. 8, a renewable oil is pumped from a storage tank and mixed with an alcohol in a specific ratio (6% to 50%) by volume. The alcohol is mixed with the oil in the pump before heating in a heat exchanger. Valves control the process flow rate and a metering pump controls the quantity of alcohol feed into the process. After heating the oil/alcohol mixture to 70-85° C., the mixture passes through two electrochemical reactors in series. Voltage is supplied to both reactors from a specially designed power unit providing square DC voltage waveforms with a 50% duty cycle. After the reaction, the product flows into an intermediate processing tank that is held for 1 hour. The product is stirred continuously at 400 RPM to allow the chain reaction to finish. The intermediate tanks are heated to maintain a constant 75° C. temperature. Two tanks allow for continuous flow through the reactors and flow is alternated between the processing tanks. Valves control flow into the tanks and pump out. After reaction in the intermediate tanks, the product is pumped to the accepts storage tank. Product is pumped from the storage tank to the acetic acid processing equipment that includes a distillation unit and a centrifuge. The products include polymer, acetic acid, glacial acetic acid, hydrocarbon, and biodiesel. Distillation removes the heavy polymer from the light distillate acetic acid, glacial acetic acid, hydrocarbon, and biodiesel. The centrifuge remove glacial acetic acid as a precipitate and the balance is hydrocarbon and/or or biodiesel. Further processing could occur by separation of the acetic acid, biodiesel, and hydrocarbon by further distillation stages (not shown), as acetic acid has a much lower temperature distillate verses hydrocarbon and biodiesel.

Example 7

Acetic Acid Manufacturing Processes

Figure 10:
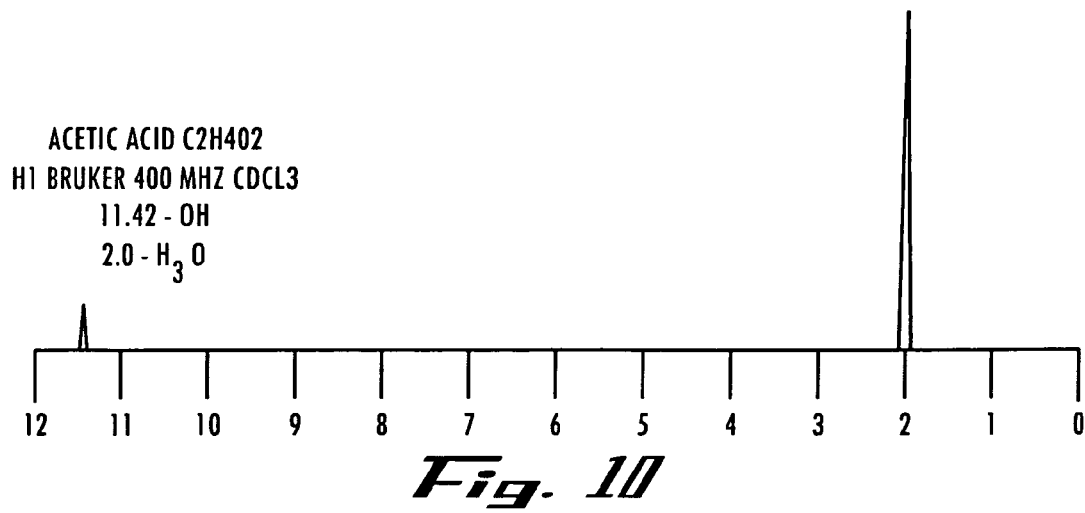
FIG. 10 is an H1 NMR spectrogram of a sample of acetic acid produced by one embodiment of the processes and devices described herein.
Figure 11:
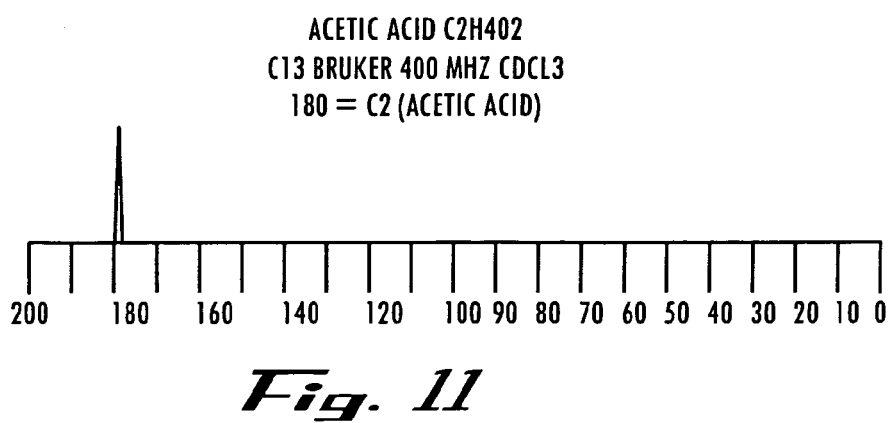
FIG. 11 is a C13 NMR spectrogram of a sample of acetic acid produced by one embodiment of the processes and devices described herein.

The process as described in Example 6 was performed and the resulting products were analyzed. NMR analysis of the distilled materials showed formation of acetic acid (glacial) when subjected to heat above 160° C. As shown in FIG. 10, the PNMR of the sample indicates H1 peaks at locations 11.42 and 2.0, indicating the presence of acetic acid. As shown in FIG. 11, the PNMR of the sample indicates a C13 peak at location 180 ppm, a slight shift from standard position at 178.9, primarily due to the excess oxygen presence in the media (biodiesel solvent). The data locates peaks at these critical locations very accurately and demonstrates the presence of glacial acetic acid.

Example 8

Fatty Acids from Biodeisel

Biodeisel was made by the process described in Example 6 and distilled. The distilled material was then subjected to NMR analysis, which showed the presence of fatty acids, predominately linoleic and oleic acids, as well as palmitic and steric acids.

Example 9

Biodiesel Fuel and $NO_X$ Emissions

Fuel tests demonstrated that biodiesel made by the process described herein is unlike conventionally made biodiesels. In one embodiment, the present methods change the fuel combustion burn rate to impact $NO_X$. A longer burn rate still provides the BTU value and lowers engine combustion temperature, thereby reducing engine $NO_X$ emissions while maintaining fuel economy. Tests show the new fuel provides a 10-25 percent improvement in fuel economy depending on driving conditions while lowering $NO_X$ emissions.

The present biodiesel production process advantageously uses am electrical charge to catalyze formation of glycerol ether in a single step process while forming esters from the triglyceride molecule. Considerable PNMR, (Proton Nuclear Magnetic Resonance) testing of the biodiesel product verifies formation of these reaction products.

Figure 7:
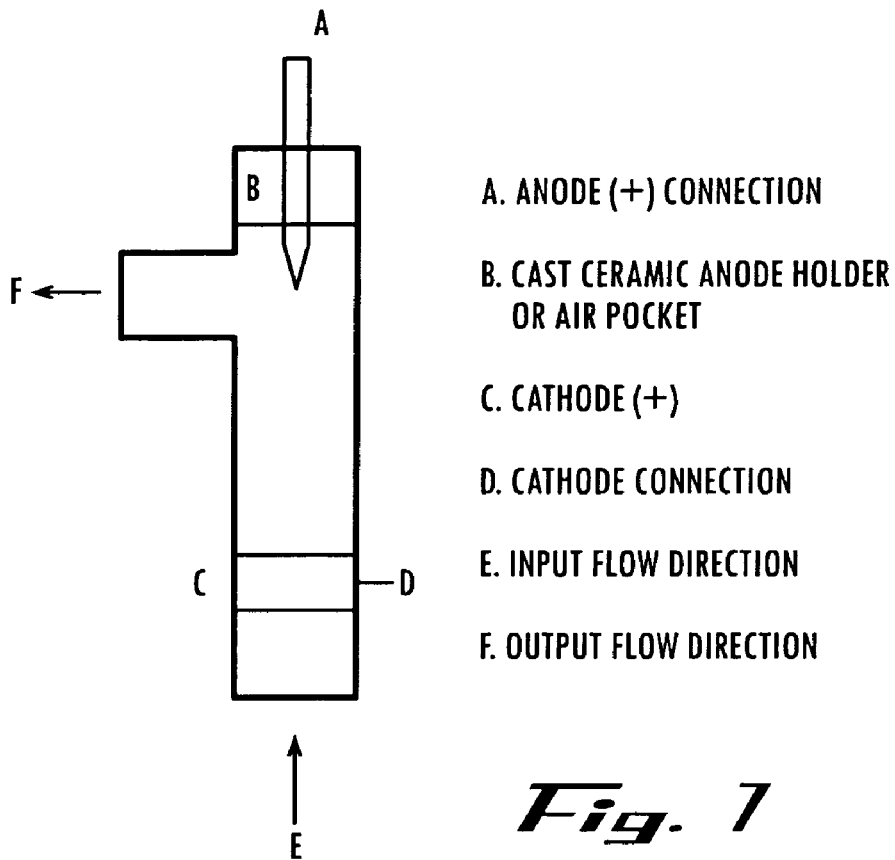
FIG. 7 is a cross-sectional view of one embodiment of a T-shaped electro-potential cell.

The biodiesel fuel tested was made using the process shown in FIG. 8 using the reactor configuration shown in FIG. 7, operating with an applied voltage of 2,300 to 4,800 volts DC. Engine emission performance and BTU (British Thermal Unit) fuel capacity testing used degummed soy bean oil. (It is contemplated that the process would produce similar results using various sources and types of vegetable/animal derived oils.) Degummed soy bean oil has a higher BTU value than refined soy bean oil, because the free fat esters are retained in the present electro-catalyzed process and improve BTU values. Degummed soy bean oil biodiesel has higher free fat esters than refined soy bean oil biodiesel using the ECR process as defined in FIG. 7.

The largest decrease in $NO_X$ was observed at engine idle. This is a significant improvement over conventional Biodiesel blends that typically test higher in $NO_X$ emissions. And is well documented by those knowledgeable in the industry. The decrease in NOX of present biodiesel is attributed due to converting the dehydrated glycerol into etherified glycerol form which act as a fuel additive in the biodiesel blend.

TABLE 2

Conventional Diesel Fuel and NOx Reduction Using New Biodiesel

| Engine/Fuel Conditions | NOx Emission (ppm) | NOx Reduction |
|---|---|---|
| Diesel Fuel - Engine at Idle | 164.92 | |
| B-20 Blend, Engine at Idle | 127.00 | 30% |
| Diesel Fuel - Engine Under Load | 370.59 | |
| B-20 Blend, Engine Under Load | 343.18 | 8% |

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for synthesizing from a renewable oil one or more chemical products selected from the group comprising mono alkyl esters and glycerol comprising the steps of:
flowing a fluid which comprises a renewable oil, an alcohol and a caustic agent through a high voltage electrical field effective to catalyze a chemical reaction to produce said one or more chemical products, wherein the high voltage electrical field is created across unobstructed fluid flow between electrodes and wherein the chemical reaction proceeds via esterification, transesterification or interesterification.

2. The method of claim 1, wherein the oil comprises a vegetable oil.

3. The method of claim 1, wherein the oil comprises an animal fat.

4. The method of claim 1, wherein the oil comprises a bio-oil.

5. A method for synthesizing mono alkyl esters from a renewable oil, comprising the steps of:
flowing a fluid which comprises a renewable oil and an alcohol through a high voltage electrical field effective to catalyze a chemical reaction to produce mono alkyl esters, wherein the high voltage electrical field is created across unobstructed fluid flow between electrodes, and wherein the weight fraction of the alcohol in the mixture of oil and alcohol flowing into the electrical field is between about 4% and about 30%.

6. The method of claim 5, wherein the weight fraction of the alcohol in the mixture of oil and alcohol flowing into the electrical field is between about 12% and about 15%.

7. The method of claim 1, wherein the fluid further comprises an acid agent.

8. The method of claim 7, wherein the caustic agent comprises sodium hydroxide or potassium hydroxide, and the acid agent is sulfuric acid hydrochloric acid, perchloric acid or combinations thereof.

9. The method of claim 1, wherein the alcohol comprises ethanol or isopropyl alcohol.

10. The method of claim 1, wherein the electric field is applied to the fluid by flowing the fluid between an anode and a cathode of an electro-potential cell.

11. The method of claim 10, wherein the electrical potential is greater than about 2,000 volts per inch between the anode and cathode.

12. The method of claim 1, wherein the electric field is generated by a direct current, pulsating direct current, pulsating bipolar current and voltage waveform, or AC waveform.

13. The method of claim 10, wherein the electro-potential cell comprises a housing in which the anode and cathode are secured, said housing having a fluid inlet through which the fluid enters the housing and a fluid outlet through which the fluid is discharged from the housing after passing through the electric field.

14. The method of claim 13, wherein the housing is cylindrical in shape, the fluid inlet having a central axis approximately coextensive with the central axis of the fluid outlet.

15. The method of claim 10, wherein the electro-potential cell comprises a P or L-shape housing in which the anode and cathode are secured, said housing having a fluid inlet through which the fluid enters the housing and a fluid outlet through which the fluid is discharged from the housing after passing through the electric field, the fluid inlet being oriented approximately perpendicular to the fluid outlet.

16. The method of claim 1, wherein the weight fraction of the alcohol in the mixture of oil and alcohol flowing into the electrical field is between about 4% and about 30%.

17. The method of claim 5, wherein the chemical reaction proceeds via esterification, transesterification or interesterification.

18. The method of claim 5, wherein the alcohol comprises methanol or ethanol and or methane gas mixture.

19. The method of claim 5, wherein the oil comprises a vegetable oil.

20. The method of claim 5, wherein the oil comprises an animal fat.

21. The method of claim 5, wherein the oil comprises a bio-oil.

22. The method of claim 5, wherein the fluid further comprises an acid agent.

23. The method of claim 22, wherein the acid agent is sulfuric acid, hydrochloric acid, perchloric acid or combinations thereof.

24. The method of claim 5, wherein the fluid further comprises an caustic agent.

25. The method of claim 24, wherein the caustic agent comprises sodium hydroxide or potassium hydroxide.

26. The method of claim 5, wherein the alcohol comprises ethanol or isopropyl alcohol.

27. The method of claim 5, wherein the electric field is applied to the fluid by flowing the fluid between an anode and a cathode of an electro-potential cell.

28. The method of claim 27, wherein the electrical potential is greater than about 2,000 volts per inch between the anode and cathode.

29. The method of claim 27, wherein the electric field is generated by a direct current, pulsating direct current, pulsating bipolar current and voltage waveform, or AC waveform.

30. The method of claim 27, wherein the electro-potential cell comprises a housing in which the anode and cathode are secured, said housing having a fluid inlet through which the fluid enters the housing and a fluid outlet through which the fluid is discharged from the housing after passing through the electric field.

31. The method of claim 27, wherein the housing is cylindrical in shape, the fluid inlet having a central axis approximately coextensive with the central axis of the fluid outlet.

32. The method of claim 27, wherein the electro-potential cell comprises a T or L-shape housing in which the anode and cathode are secured, said housing having a fluid inlet through which the fluid enters the housing and a fluid outlet through which the fluid is discharged from the housing after passing through the electric field, the fluid inlet being oriented approximately perpendicular to the fluid outlet.

33. The method of claim 1, wherein the renewable oil is in the crude form.

34. The method of claim 5, wherein the renewable oil is in the crude form.

* * * * *

UNITED STATES PATENT AND TRADEMARK OFFICE
CERTIFICATE OF CORRECTION

PATENT NO.       : 7,722,755 B2
APPLICATION NO.  : 10/987115
DATED            : May 25, 2010
INVENTOR(S)      : J. Alan Lawson and Ahmed A. Baosman It is certified that error appears in the above-identified patent and that said Letters Patent is hereby corrected as shown below:

At column 27, line 62, after "comprises a" delete "P" and insert --T--.

Signed and Sealed this

Seventh Day of December, 2010

David J. Kappos
*Director of the United States Patent and Trademark Office*